(12) United States Patent
Sykes

(10) Patent No.: US 11,284,607 B2
(45) Date of Patent: Mar. 29, 2022

(54) GENETIC MODIFICATION OF PIGS FOR XENOTRANSPLANTATION

(71) Applicant: The Trustees of Columbia University in the City of New York, New York, NY (US)

(72) Inventor: Megan Sykes, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 669 days.

(21) Appl. No.: 15/558,789

(22) PCT Filed: Mar. 23, 2016

(86) PCT No.: PCT/US2016/023763
§ 371 (c)(1),
(2) Date: Sep. 15, 2017

(87) PCT Pub. No.: WO2016/154299
PCT Pub. Date: Sep. 29, 2016

(65) Prior Publication Data
US 2018/0070564 A1 Mar. 15, 2018

Related U.S. Application Data

(60) Provisional application No. 62/137,544, filed on Mar. 24, 2015.

(51) Int. Cl.
*A01K 67/027* (2006.01)
*A61K 35/12* (2015.01)
(Continued)

(52) U.S. Cl.
CPC .......... *A01K 67/0276* (2013.01); *A61K 35/12* (2013.01); *A61K 35/28* (2013.01);
(Continued)

(58) Field of Classification Search
CPC ............ A01K 67/0275; A01K 2217/20; A01K 2227/108; A61K 2035/122
See application file for complete search history.

(56) References Cited

U.S. PATENT DOCUMENTS

2002/0150556 A1* 10/2002 Vile et al. .............. A61K 48/00
424/93.2
2004/0143874 A1 7/2004 Moller et al.
(Continued)

OTHER PUBLICATIONS

Hasan et al. "A human sleep homeostasis phenotype in mice expressing a primate-specific PER3 variable-number tandem-repeat coding-region polymorphism", FASEB J. Jun. 2014; 28(6): 2441-2454 (first published Feb. 2014). (Year: 2014).*
(Continued)

*Primary Examiner* — James D Schultz
*Assistant Examiner* — James Joseph Graber
(74) *Attorney, Agent, or Firm* — Leason Ellis LLP

(57) ABSTRACT

The invention provides for transgenic donor animals (e.g., pigs) whose cells, tissues and organs have a better long-term survival when transplanted into a human patient. The transgenic donor animal carries one or more human transgenes which is expressed only when the endogenous gene of the donor animal is knocked out shortly before a graft is harvested for transplantation. This "genetic switch" allows the donor animal to remain healthy during the majority of its lifetime, while still allowing expression of the human transgene for optimal transplant tolerance in a human recipient. The transgene may encode a cytokine receptor, an adhesion molecule, or a complement regulatory protein.

12 Claims, 1 Drawing Sheet

Specification includes a Sequence Listing.

(51) Int. Cl.
*A61K 35/28* (2015.01)
*C12N 5/0789* (2010.01)
*C12N 5/077* (2010.01)

(52) U.S. Cl.
CPC ......... *C12N 5/0647* (2013.01); *C12N 5/0669* (2013.01); *A01K 2217/054* (2013.01); *A01K 2217/075* (2013.01); *A01K 2217/203* (2013.01); *A01K 2217/206* (2013.01); *A01K 2227/108* (2013.01); *A01K 2267/025* (2013.01); *A61K 2035/124* (2013.01)

(56) References Cited

U.S. PATENT DOCUMENTS

| | | | |
|---|---|---|---|
| 2006/0057719 | A1 | 3/2006 | Denning et al. |
| 2008/0250517 | A1 | 10/2008 | Colman et al. |
| 2014/0017215 | A1 | 1/2014 | Ayares |
| 2015/0017130 | A1 | 1/2015 | Yang et al. |

OTHER PUBLICATIONS

Dwyer et al. "Thromboregulatory manifestations in human CD39 transgenic mice and the implications for thrombotic disease and transplantation", J. Clin. Invest. 113:1440-1446 (2004). (Year: 2004).*
Alisky "Xenografts are an achievable breakthrough", Medical Hypotheses (2004) 63, 92-97. (Year: 2004).*
Schnutgen et al. "Engineering Embryonic Stem Cells with Recombinase Systems", Methods in Enzymology, vol. 420:100-136, 2006. (Year: 2006).*
Prather et al., "Genetically Engineered Pig Models for Human Diseases", Annu. Rev. Anim. Biosci. 2013. 1:203-219. (Year: 2013).*
Zou et al. "Cre-loxP-mediated gene replacement: a mouse strain producing humanized antibodies", Current Biology, 1994, vol. 4, No. 12, pp. 1099-1103. (Year: 1994).*
Yang et al. "CD47 in xenograft rejection and tolerance induction", Xenotransplantation 2010: 17: 267-273. (Year: 2010).*
Ide et al. "Role for CD47-SIRPα signaling in xenograft rejection by macrophages" PNAS 2007, vol. 104, No. 12, 5062-5066. (Year: 2007).*
Hui Wang et al. "The Transmembrane Domains of Ectoapyrase (CD39) Affect Its Enzymatic Activity and Quaternary Structure" Journal of Biological Chemistry, vol. 273, Issue 38, 1998, pp. 24814-24821. (Year: 1998).*
Koike et al. "Direct gene replacement of the mouse α(I,3)-galactosyltransferase gene with human α(I,2)-fucosyltransferase gene: Converting α-galactosyl epitopes into H antigens" Xenotransplantation 1997, 4:147-153. (Year: 1997).*
Domino et al. "Deficiency of Reproductive Tract α(1,2)Fucosylated Glycans and Normal Fertility in Mice with Targeted Deletions of the FUT1 or FUT2 α(1,2)Fucosyltransferase Locus" Molecular and Cellular Biology, 2001, vol. 21, No. 24, p. 8336-8345. (Year: 2001).*
Aigner et al. "Transgenic pigs as models for translational biomedical research" J Mol Med (2010) 88:653-664. (Year: 2010).*
Loi et al. "A New, Dynamic Era for Somatic Cell Nuclear Transfer?" Trends in Biotechnology, vol. 34, No. 10 (published online: Apr. 22, 2016). (Year: 2016).*
International Search Report and Written Opinion dated Jun. 30, 2016 corresponding to International Patent Application No. PCT/US2016/023763; 17 pages.
Griesemer et al. "Xenotransplantation: Immunological Hurdles and Progress Toward Tolerance," Immunological Reviews, Mar. 1, 2014 (Mar. 1, 2014), vol. 258, pp. 241-258.
Sachs et al. "Acheiving Tolerance in Pig-to-Primate Xenotransplantation: Reality or Fantasy," Transplant Immunology, Jun. 30, 2009 (Jun. 30, 2009), vol. 21, pp. 101-105.
Ide, Kenaro et al., "Role for CD47-SIRPα signaling in xenograft rejection by macrophages", PNAS, Mar. 20, 2007, vol. 104, No. 12, pp. 5062-5066.
Wang, Hui et al., "Attenuation of phagocytosis of xenogeneic cells by manipulating CD47", Blood, Jan. 15, 2007, vol. 109, No. 2.

* cited by examiner

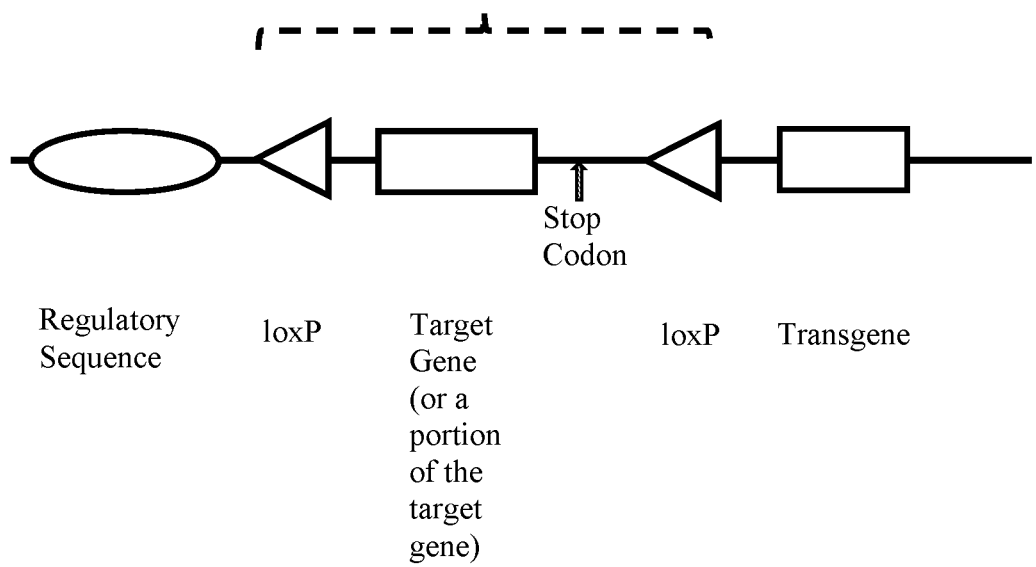

SEQUENCE LISTING

<160> NUMBER OF SEQ ID NOS: 2

<210> SEQ ID NO 1
<211> LENGTH: 34
<212> TYPE: DNA
<213> ORGANISM: artificial sequence
<220> FEATURE:
<223> OTHER INFORMATION: synthetic sequence

<400> SEQUENCE: 1
ataacttcgt atagcataca ttatacgaag ttat                    34

<210> SEQ ID NO 2
<211> LENGTH: 34
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (14)..(16)
<223> OTHER INFORMATION: n is a, c, g, or t
<220> FEATURE:

```
<221> NAME/KEY: misc_feature
<222> LOCATION: (19)..(21)
<223> OTHER INFORMATION: n is a, c, g, or t

<400> SEQUENCE: 2
ataacttcgt atannntann ntatacgaag ttat                               34
```

GENETIC MODIFICATION OF PIGS FOR XENOTRANSPLANTATION

CROSS REFERENCE TO RELATED APPLICATIONS

This application claims priority to U.S. Provisional Application No. 62/137,544 (filed on Mar. 24, 2015), which is incorporated herein by reference in its entirety.

FIELD OF THE INVENTION

The present invention relates to making and using transgenic pigs for xenotransplantation in a patient.

BACKGROUND

The severe shortage of allogeneic donors currently limits the number of organ transplants performed. This supply-demand disparity may be corrected by the use of organs from other species (xenografts). In view of the ethical issues and impracticalities associated with the use of non-human primates, pigs are considered the most suitable donor species for humans. In addition to organ size and physiologic similarities to humans, the ability to rapidly breed and inbreed pigs makes them particularly amenable to genetic modifications that could improve their ability to function as graft donors to humans (Sachs, Path. Biol. 42:217-219, 1994; Piedrahita et al., Am. J. Transplant, 4 Suppl. 6:43-50, 2004).

Although transplantation coupled with non-specific immunosuppressive therapy is associated with high early graft tolerance, a major limitation to the success of clinical organ transplantation has been late graft loss, due largely to chronic rejection of the transplant.

Immune tolerance is more important for successful clinical xenotransplantation, as the level of life-long immunosuppression required to prevent xenograft rejection can be too toxic to be acceptable. In addition, no markers have been identified to reliably indicate whether or not immunological tolerance has been achieved in patients, resulting in an absence of laboratory parameters upon which to base immunosuppression withdrawal.

Therefore, goals in xenotransplantation include optimizing the durability of mixed chimeric cells originated from the donor animal after they are transplanted into a xenogeneic recipient, as well as maintaining the health and viability of the donor animal.

Mixed chimerism can induce tolerance to the donor at the level of T cells, B cells and natural killer (NK) cells in the recipient. Griesemer A., Yamada K. and Sykes M., Xenotransplantation: Immunological hurdles and progress toward tolerance, Immunol. Rev. 2014, 258(1): 241-258. Sachs D. H., Kawai T. and Sykes M., Cold Spring Harb. Perspect. Med. 2014; 4:a015529. Hematopoiesis is a tightly regulated process involving interactions of cytokines and adhesion molecules in the bone marrow microenvironment with receptors on the hematopoietic cells. Because many of these receptor-ligand interactions are species-specific (e.g., IL-3 and IL-3R) or species-selective (e.g., SCF-cKIT, GM-CSF-GM-CSFR, VLA-5-fibronectin), mixed chimeric cells (e.g., from a pig) will be at a competitive disadvantage compared to endogenous hematopoietic cells (e.g., human cells), resulting in a gradual loss of the transplanted cells. Since durable mixed chimerism can best assure life-long T, B and NK cell tolerance, this loss of chimerism is undesirable.

Introduction of human cytokine receptors and adhesion molecules into a porcine donor animal would help to overcome this competitive disadvantage, assuring lifelong chimerism and tolerance. Griesemer A., Yamada K. and Sykes M., Xenotransplantation: Immunological hurdles and progress toward tolerance, Immunol. Rev. 2014, 258(1): 241-258. Because hematopoiesis is tightly regulated, it may be desirable to insert these genes into their natural locus in the porcine genome so they can function in a physiologic manner under the control of the native regulatory sequence. This may be achieved by disrupting the native porcine gene and replacing it with the human counterpart. However, this approach can have the problem of rendering porcine cells unresponsive or hyporesponsive to species-specific or species-selective porcine cytokines (or adhesion ligands), respectively. Therefore, long-term expression of human transgenes can be deleterious to the health of the donor animal. Dwyer et al., Thromboregulatory manifestations in human CD39 transgenic mice and the implications for thrombotic disease and transplantation, J. Clin. Invest. 2004 May; 113(10):1440-6. Crikis et al., Anti-inflammatory and anticoagulant effects of transgenic expression of human thrombomodulin in mice, Am. J. Transplant, 2010 February; 10(2):242-50.

SUMMARY

The present application provides for a method of supplying a graft from a donor mammal of a first species for transplant in a recipient mammal of a second species. The method may comprise the steps of: (a) inducing knockout of at least one conditional knockout allele of a target gene in the donor mammal, wherein the knockout of the target gene results in expression of a transgene of the second species, the transgene being a homolog of the target gene of the first species, and wherein the transgene is expressed under the control of the native regulatory sequence of the target gene when the target gene (or a portion of the target gene) is knocked out; and (b) providing a graft from the donor mammal for transplant.

Also encompassed by the present application is a transgenic mammal of a first mammalian species, comprising: a) at least one conditional knockout allele of a target gene of the first mammalian species, at its natural genomic locus of the mammal of the first mammalian species, and b) a transgene of a second mammalian species, wherein the transgene is a homolog of the target gene of the first mammalian species, wherein the transgene is located downstream from the conditional knockout allele of the target gene, and wherein the transgene is expressed under the control of the native regulatory sequence of the target gene when the target gene is knocked out.

The first species may be swine, such as a miniature swine. The second species may be human.

The present application also provides for a method of supplying a graft from a donor swine for transplant in a human recipient. The method may comprise the steps of: (a) inducing knockout of at least one conditional knockout allele of a target gene in the donor swine, wherein the knockout of the target gene (or a portion of the target gene) results in expression of a human transgene, the human transgene being a homolog of the swine target gene, and wherein the human transgene is expressed under the control of the native regulatory sequence of the swine target gene when the swine target gene (or a portion of the target gene) is knocked out; and (b) providing a graft from the donor swine for transplant.

The engineered target gene in the donor mammal (e.g., a donor swine) may contain homozygous conditional knockout alleles or heterozygous conditional knockout alleles. For example, in step (a) of the present methods of supplying a graft, homozygous conditional knockout alleles of the target gene may be knocked out.

The conditional knockout allele of the target gene may comprise a nucleic acid sequence at least 90%, at least 95%, at least 96%, at least 97%, at least 98%, at least 99%, or 100% identical to the sequence of the wildtype allele (or a portion of the wild type allele) of the target gene of the first species (e.g., a swine).

The target gene/transgene may encode a cytokine, a cytokine receptor, an adhesion molecule, and/or a complement regulatory protein. Non-limiting examples of the target gene/transgene include IL-3 receptor, IL-3, CD47, thrombomodulin, CD39, CD200, a ligand for paired Ig-like receptor (PIR)-B, a ligand for immunoglobulin-like transcript (ILT)3, a ligand for CD33-related receptors, CD46 (MCP), CD55 (DAF), CD59, IL-4, IL-6, IL-10, IL-11, GM-CSF, G-CSF, Epo, Tpo, Flt-3L, SCF, M-CSF, MSP and the HLA-E/beta2 microglobulin/human leader peptide trimer.

The conditional knockout allele may be flanked by two LoxP sequences and may be knocked out by an inducible Cre recombinase. In one embodiment, the LoxP sequences are SEQ ID NO:1 or SEQ ID NO:2.

The expression of the inducible Cre recombinase may be under the control of an inducible promoter. In one embodiment, the inducible promoter is induced by a drug. Alternatively, the Cre recombinase may be induced by translocating to the nucleus of a cell upon addition of a drug.

Drugs that may be used to induce the Cre recombinase include, but are not limited to, doxycycline, tetracycline, RU486, and tamoxifen.

The graft may comprise cells, a tissue and/or an organ. For example, the graft may comprise a heart, a kidney, a liver, a pancreas, a lung, an intestine, skin, a small bowel, a trachea, a cornea, or combinations thereof. In one embodiment, the graft comprises hematopoietic stem cells. In another embodiment, the graft comprises bone marrow.

The present application provides for a cell (e.g., a hematopoietic stem cell), a tissue (e.g., bone marrow), and/or an organ from the transgenic mammal. The organ may be a heart, a kidney, a liver, a pancreas, a lung, an intestine, skin, a small bowel, a trachea, a cornea, and combinations thereof.

The present application also provides for a method for making a transgenic mammal of a first species, the method comprising the steps of: (a) replacing at least one allele of an endogenous target gene of the first species with a conditional knockout allele of the target gene, and (b) inserting a transgene from a second species downstream from the conditional knockout allele of the target gene, wherein the transgene is a homolog of the target gene of the first species, and wherein the transgene is expressed under the control of the native regulatory sequence of the target gene when the target gene is knocked out. The method may further comprise a step (c) of somatic cell nuclear transfer. In one embodiment, the somatic cell is a fibroblast from the first species.

The first species may be swine, such as a miniature swine. The second species may be human.

BRIEF DESCRIPTION OF THE FIGURE

FIG. 1 depicts how the transgenes are arranged on the porcine genome in an embodiment of the invention.

DETAILED DESCRIPTION

The present invention provides for transgenic donor animals (e.g., pigs) whose cells, tissues and organs have a better long-term survival when transplanted into a human patient. The transgenic donor animal carries a human transgene which is expressed only when the endogenous gene of the donor animal is knocked out shortly before a graft is harvested for transplantation. This "genetic switch" allows the donor animal to remain healthy during the majority of its lifetime, while still permitting expression of the human transgene for optimal transplant tolerance in a human recipient.

The endogenous gene ("target gene") of the transgenic donor animal exists in the form of homozygous or heterozygous conditional knockout alleles each of which is flanked by recombinase recognition sites. The human transgene is a homolog of the target gene of the donor animal, and may be knocked in downstream from the conditional knockout allele of the target gene (FIG. 1). Full-length or a portion of the human transgene may be knocked in to the donor animal for expressing a functional protein/polypeptide, when the target gene (or a portion of the target gene) is knocked out.

During the majority of its lifetime, the transgenic donor animal expresses its endogenous gene and functions normally. Prior to transplantation, the donor animal's target gene is knocked out, by, e.g., an inducible recombinase, so that the downstream human transgene is now expressed under the control of the native regulatory sequence of the target gene of the donor animal. Due to expression of the human transgene, a graft from the donor animal experiences less transplant rejection in a human recipient. The donor animal may carry one or more human transgenes, with their respective homolog gene in the donor animal ("target genes") modified to contain at least one conditional knockout allele. The graft may be bone morrow, hematopoietic stem cells, or any suitable cells, tissues or organs.

The transgene of the second species (e.g. human) may be expressed (e.g., conditionally) under the control of a heterologous promoter, and/or a constitutive promoter.

The target gene/transgene may encode a cytokine receptor, a cytokine, an adhesion molecule, or a complement regulatory protein. Non-limiting examples of the proteins/polypeptides encoded by the target gene/transgene include, IL-3 receptor (IL-3R), IL-3 (Interleukin-3), CD47, thrombomodulin, CD39, CD200, c-kit, a ligand for paired Ig-like receptor (PIR)-B, a ligand for immunoglobulin-like transcript (ILT)3, a ligand for CD33-related receptors, CD46 (MCP), CD55 (DAF), CD59, (Interleukin-4), IL-6 (Interleukin-6), IL-10 (Interleukin-10), IL-11 (Interleukin-11), GM-CSF (granulocyte-macrophage colony-stimulating factor), GM-C SF receptor, G-C SF (granulocyte-colony stimulating factor), erythropoietin (EPO), TPO (thrombopoietin), Flt-3L (FMS like tyrosine kinase 3 ligand), SCF (stem cell factor), M-CSF (macrophage colony-stimulating factor), MSP (macrophage stimulating factor) and the HLA-E/beta2 microglobulin/human leader peptide trimer.

The inducible recombinase may be knocked in the transgenic donor animal as part of a drug-responsive gene cassette which expresses a functional recombinase when the drug, such as tamoxifen or tetracycline, is administered to the transgenic donor animal. The drug may be given shortly before harvest of a graft from the transgenic donor animal.

The target gene of the donor animal may be knocked out and the human transgene expressed about 6 months, about 5 months, about 4 months, about 3 months, about 2 months, about 1 month, about 4 weeks, about 3 weeks, about 2 weeks, about 1 week, about 6 days, about 5 days, about 4 days, about 3 days, about 2 days, or about 1 day, prior to harvesting one or more grafts for transplantation.

The invention is related to methods and transgenic donor animals for controlling the timing of transgene expression in the transgenic donor animals to prevent or minimize deleterious effects associated with long-term expression of the transgene in the donor animal. In one embodiment, the transgene is inserted into the natural locus of its homolog (which is the target gene) in the transgenic donor animal and downstream from the target gene. Thus, when the target gene is knocked out, the expression of the transgene will be under the control of the native regulatory sequence of the target gene.

This genome engineering may take advantage of homologous recombination (HR) between a cellular DNA and an exogenous DNA (e.g., a DNA construct, a vector, etc.) introduced into the cell. Preferably, the sequence-specific insertion (knock-in) of one or more transgenes (e.g., conditional knockout alleles, recombinase recognition sites, recombinase, and/or a human transgene) into the genome of the donor species may be achieved by a sequence-specific endonuclease coupled with homologous recombination (HR) of the targeted DNA with an exogenous DNA (e.g., a DNA construct, a vector, etc.) containing the transgene(s).

Alternatively, the human transgene, together with all of its necessary regulatory sequence, is introduced into the donor animal, for example as a human artificial chromosome.

The first mammalian species (i.e., the donor) may be a non-human mammalian species, such as a swine species (e.g., a miniature swine species) or a non-human primate species. Non-limiting examples of the first mammalian species include a swine, rodent, non-human primate, cow, goat, and horse.

In one embodiment, the first mammalian species is a miniature swine which is at least partially inbred (e.g., the swine is homozygous at swine leukocyte antigen (SLA) loci, and/or is homozygous at at least 65%, 70%, 75%, 80%, 85%, 90%, 95%, or more, of all other genetic loci). The genetic engineering can be made in wholly or partially inbred swine (e.g., miniature swine, transgenic swine, etc.). For example, inbred Massachusetts General Hospital (MGH) miniature swine may be used in the present methods. These include the MGH miniature swine which have been inbred for over 40 years and are homozygous at all genetic loci. In one embodiment, inbred $SLA^{dd}$ miniature swine may be used. Mezrich et al. and Sachs, Histocompatible miniature swine: An inbred large-animal model. Transplantation, 2003; 75:904-907. Swine at National Swine Resource and Research Center (NSRRC, RADIL, University Missouri, Columbia Mo.) may also be used in the present methods.

In one embodiment, the second species is human.

In various embodiments, the donor (first species) and recipient (second species) are of different species. For example, the donor is a non-human animal, e.g., a miniature swine, and the recipient is a human.

The present invention provides for a transgenic mammal of a first mammalian species, the transgenic mammal comprising: (a) at least one conditional knockout allele of a target gene of the first mammalian species, located at its natural genomic locus of the mammal; and (b) a transgene of a second mammalian species, wherein the transgene is a homolog of the target gene of the first mammalian species, wherein the transgene is located downstream from the conditional knockout allele of the target gene, and wherein the transgene is expressed under control of the native regulatory sequence of the target gene when the target gene (or a portion of the target gene, or a portion of an allele of the target gene) is knocked out. The first mammalian species may be swine including a miniature swine. The second mammalian species may be human.

In one embodiment, the human transgene is knocked in downstream from the conditional knockout allele of the target gene. At least one stop codon, located downstream from the conditional knockout allele of the target gene and upstream of the human transgene, prevents expression of the human transgene (FIG. 1). When the target gene (or a portion of the target gene, a portion of an allele of the target gene) is knocked out together with the stop codon, the human transgene will be expressed under the control of the natural regulatory sequence of the target gene.

A regulatory sequence of a gene may refer to a segment (or segments) of DNA which is capable of increasing or decreasing transcription of the gene with which they are operably linked. A regulatory sequence of a gene may include one or more elements of an enhancer(s), a silencer(s), a promoter, the 5' untranslated region (5' UTR) and the 3' untranslated region (3' UTR).

In certain embodiments, when the target gene (or a portion of the target gene, or a portion of an allele of the target gene) is knocked out of the first species, transcription of the transgene is under the control of a regulatory sequence which naturally controls the expression of the target gene in the first species. Alternatively, the transgene can be under the control of regulatory sequences different from those sequences naturally controlling transcription of the target gene in the first species. For example, transcription of the transgene can be under the control of a synthetic promoter sequence. The promoter that controls transcription of the transgene may be of viral origin; examples are promoters derived from bovine herpes virus (BHV), Moloney murine leukemia virus (ML V), SV 40, Swine vesicular disease virus (SVDV), and cytomegalovirus (CMV).

Also encompassed by the present invention are methods of transplanting a graft from such a donor animal of the first mammalian species into a mammal of a second mammalian species (e.g., human).

The present invention provides for a method of supplying a graft from a donor mammal of a first species for transplant in a recipient mammal of a second species. The method may contain the following steps: (a) inducing knockout of at least one conditional knockout allele of a target gene (or a portion of the target gene, or a portion of an allele of the target gene) in the donor mammal, wherein the knockout of the target gene results in expression of a transgene of the second species, the transgene being a homolog of the target gene of the first species, and wherein the transgene is expressed under the control of the native regulatory sequence of the target gene when the target gene is knocked out; and (b) providing a graft from the donor mammal for transplant. The first mammalian species may be swine including a miniature swine. The second mammalian species may be human.

The present invention further provides for a method for making a transgenic mammal of a first species. The method may contain the following steps: (a) replacing at least one allele of an endogenous target gene of the first species with a conditional knockout allele of the target gene, and (b) inserting a transgene from a second species downstream from the conditional knockout allele of the target gene, the transgene being a homolog of the target gene of the first species, and wherein the transgene is expressed under the control of the native regulatory sequence of the target gene when the target gene is knocked out.

One allele, or both alleles, of a target gene of the first species may be replaced with a conditional knockout allele, or two conditional knockout alleles, of the target gene.

In a further aspect, a method of generating a conditional knock-out animal is provided, the method comprising the steps of: (a) introducing a gene cassette into a cell, the gene cassette comprising a 5' homology region, a 5' recombinase recognition site, a target gene sequence, a 3' recombinase recognition site, and a 3' homology region; (b) introducing a sequence-specific endonuclease into the cell, wherein the endonuclease cleaves the target gene of the genome of the cell; and (c) introducing the cell into a carrier animal to produce the conditional knock-out animal.

An alternative approach is to introduce a human cytokine transgene and the corresponding cytokine receptor transgene in their corresponding genomic loci into the donor animal. This may ensure that hematopoiesis functions normally under the control of the cytokine in both the donor animal and in human after transplantation.

The modified DNA sequence that is introduced into the donor animal genome may contain one or more marker or reporter genes. A marker gene may be a gene that confers resistance to a certain toxic agent (e.g., a neomycin-resistance gene) or that produces an observable change (e.g. color or fluorescence). The marker or reporter gene may be flanked by recombinase recognition sites for subsequent activation, inactivation, or deletion. In one embodiment, a marker gene is incorporated between the two recombinase recognition sites (e.g., loxP sites) and can be knocked out together with the donor target gene by an inducible recombinase.

The transgenic animal may be produced through genomic modification of somatic cells in vitro followed by somatic cell nuclear transfer (SCNT). In this process, the nuclei of somatic cells are transferred into enucleated oocytes (e.g., metaphase II oocytes), and then this complex is activated (e.g., by electrofusion). Reconstructed embryos are then cultured and introduced into a female carrier animal to produce transgenic animals. U.S. Pat. No. 7,135,608. In certain embodiments, the cell is expanded to a two-cell stage, introduced into a blastocyst, or otherwise cultured or associated with additional cells prior to introduction into the carrier animal.

When donor animals heterozygous for the conditional knockout allele and/or the human transgene allele are generated, they can be interbred to produce offspring homozygous for the conditional knockout allele and/or the human transgene allele.

To generate homozygous alleles, both alleles of the target gene may be targeted at the same time in cells in vitro before SCNT. Alternatively, cells are engineered to contain heterozygous alleles where the wildtype allele can further be targeted to generate homozygous alleles.

To test whether desired DNA sequences (e.g., transgenes, recombinase recognition sites, etc.) have been incorporated into a cell or an animal's genome, any suitable techniques can be used, such as sequencing, PCR (polymerase chain reaction), Southern blot, etc. Expression of a gene can also be tested, such as RT-PCR coupled with sequencing, Northern blot to study RNAs, and antibodies to assay proteins. The functionality of a peptide or protein can also be assessed by methods well-known in the art, such as functional assays, enzymatic assays, and biochemical assays.

Conditional Knockout

A conditional (or inducible) knockout allows the target gene to be inactivated in a time-specific or tissue-specific manner. For example, the target gene is expressed for the majority of the donor animal's lifetime, and is inactivated just prior to the harvest of cells, tissues and/or organs for transplantation. The health of the transgenic donor/host animal is improved by limiting expression of the xenogeneic transgene to a relatively short period of time before grafts are harvested from the donor animal for transplantation.

A number of sequence-specific recombination system (or recombinase-mediated cassette exchange (RMCE)) systems may be used to achieve conditional knockout, such as the Cre-lox, Flp-frt, or Dre-rox systems. Any other suitable systems may also be used. In one embodiment, conditional knockouts are constructed so that they are inducible, such as by using a modified form of a recombinase that is non-functional until a drug is administered.

Sequence-Specific Recombination

A sequence-specific recombination system may be used to achieve the conditional knockout of the target gene. The recombinase is an enzyme that recognizes specific polynucleotide sequences (recombinase recognition sites) that flank an intervening polynucleotide and catalyzes a reciprocal strand exchange, resulting in inversion or excision of the intervening polynucleotide. Araki et al., Proc. Natl. Acad. Sci. USA 92:160-164 (1995).

For example, conditional knock-out alleles may include recombinase recognition sequences (sites) that flank the target gene (or a portion(s) of the target gene) but leaves the gene's function intact or substantially unchanged, such that the conditional knockout allele produces functional proteins/polypeptides substantially similar to the unmodified allele. The functional protein/polypeptide may comprise the full-length protein/polypeptide encoded by the wildtype allele of the target gene, or may comprise a fragment of the full-length protein/polypeptide encoded by the wildtype allele of the target gene. The conditional knock-out allele can be rendered non-functional at a certain time or within certain tissues by the presence of the functional recombinase recognizing the recognition sequences.

The recombinase recognition sequences are nucleic acid sequences that are recognized by a recombinase which subsequently catalyzes recombination at the recombination recognition sites. Examples of recombinase recognition sites include loxP (locus of X-over P1) sites (Hoess et al., Proc. Natl. Acad. Sci. USA 79:3398-3401 (1982)), frt sites (McLeod, M., Craft, S. & Broach, J. R., Molecular and Cellular Biology 6, 3357-3367 (1986)) and rox sites (Sauer, B. and McDermott, J., Nucleic Acids Res 32, 6086-6095 (2004)). Therefore, any of the following systems may be used: loxP sites and Cre recombinase; frt sites and flippase (FLP) recombinase; and rox sites and Dre recombinase.

Examples of recombinases suitable for use in the methods also include any inducible version of the recombinases, such as a recombinase fused to a hormone-responsive domain such as CreERT2 and Cre-PR, or tetracycline-regulated recombinase.

The orientation and location of the recombinase recognition sites, where the recombination takes place, can be manipulated to produce a system which deletes, translocates or inverts the sequence between the recombinase recognition sites. If the recombinase recognition sites are oriented in opposite directions, the recombinase catalyzes the inversion of the segment between the recombinase recognition sites. If the recombinase recognition sites are located on different chromosomes, the segment between the recombinase recognition sites is translocated. In certain embodiments of the present invention, the recombinase recognition sites are oriented in the same direction on a DNA strand, and the segment is deleted by the recombinase.

In one embodiment, for a conditional knockout of a target gene of donor animal (e.g., a pig or other species), the Cre-loxP system may be used. This involves targeted integration (knock-in) of loxP sites via homologous recombination (HR) and the expression of inducible Cre recombinase. For example, each LoxP site can be a 34-bp sequence which contains an 8-bp core sequence and two flanking 13 bp inverted repeats (ATAACTTCGTATAGCATACAT-TATACGAAGTTAT; SEQ ID NO:1). The LoxP site may also comprise the following sequence: ATAACTTCGTA-TANNNTANNNTATACGAAGTTAT (SEQ ID NO:2) where "N" indicates bases which may vary. Other LoxP sites may also be used. Missirlis et al., (2006). "A high-throughput screen identifying sequence and promiscuity characteristics of the loxP spacer region in Cre-mediated recombination". BMC Genomics 7: 73. Livet et al., Transgenic strategies for combinatorial expression of fluorescent proteins in the nervous system, Nature 450, 56-62 (2007).

Inducible Recombinase

Conditional expression of the transgene (which encodes, e.g., a recombinase, or a xenogeneic transgene such as a human transgene) can be achieved by using regulatory sequence that can be induced or inactivated by exogenous stimuli. For example, the sequence-specific recombination system of the conditional knock-out allele can be regulated, by, e.g., having the activity of the recombinase to be inducible by a chemical (drug). The chemical may activate the transcription of the Cre recombinase gene, or activates transport of the Cre recombinase protein to the nucleus. Alternatively, the recombinase can be activated by the absence of an administered drug rather than by its presence.

In one embodiment, the recombinase gene is under the control of a tissue-specific promoter or an inducible promoter.

In another embodiment, Cre is fused with a mutated ligand binding domain of human estrogen receptor ERT2. 4-hydroxytamoxifen (4OHT) is then used to control Cre activity by promoting Cre-ERT2 fusion protein translocation from the cytoplasm to the nucleus where Cre recognizes and recombines loxP sites embedded in the genomic DNA. Feil et al, (1997) Regulation of Cre recombinase activity by mutated estrogen receptor ligand-binding domains. Biochem. Biophys. Res. Commun. 237, 752-757.

Non-limiting examples of the chemicals regulating the inducible system (thus, e.g., inducing conditional knockouts) include tetracycline, tamoxifen, RU-486, doxycycline, and the like. Nagy A (February 2000), Cre recombinase: the universal reagent for genome tailoring, Genesis, 26 (2): 99-109.

In an embodiment of the transgenic animal, such as a humanized pig, expression of the pig endogenous gene is conditional on the absence of a drug, so that administering the drug activates a genetic switch that deletes/knocks out the pig gene and permits expression of the human transgene. This is timed just prior to harvesting the donor tissue or cells so that the transplanted mixed chimeric cells and tissues can function optimally in the human transplant recipient.

In certain embodiments, the transgene encoding the recombinase is under the control of a tissue-specific promoter, such that the recombinase is expressed and, consequently, the gene is knocked out, only in such tissue. In some embodiments, the transgene encoding the recombinase is under the control of an inducible promoter, such that recombinase expression can be induced at a specific time. For example, the activation of Tet-On or Tet-Off promoters can be controlled by tetracycline or one of its derivatives. In some embodiments, the recombinase-encoding transgene is expressed only at a certain stage of development or in response to a compound administered to the animal.

In a third embodiment, the tetracyclin-regulated Tet-On and Tet-Off systems are used. In one embodiment, all elements of this system (e.g., expression of the tetracycline-dependent transactivator and the transactivator-dependent expression of the transgene) are combined in a single construct. Transgenic donor animals are produced with a construct containing an autoregulatory bicistronic Tet-Off-based expression cassette, where the transactivator responsive promoter (PtTA) drives the cDNA for the recombinase. Via a poliovirus IRES, this was linked with a Tet-Off transactivator (tTA). Minimal expression of the Tet-Off transactivator promoter results in tTA expression and binding to the transactivator responsive promoter PtTA which initiates an auto-regulative loop. In the presence of exogenous doxycycline, the transactivator tTA is inactivated and recombinase gene transcription is silenced. Klymiuk et al., Genetic Modification of Pigs as Organ Donors for Xenotransplantation, Molecular Reproduction & Development 77:209-221 (2010).

Conditional expression of the xenogeneic transgene (e.g., human transgene) in the donor animal may be dependent on the knockout of the endogenous donor target gene, or may be induced by exogenous stimuli.

Genetic Modification of Cells In Vitro

The genome of the donor animal may be modified by (i) making expression of the target gene of the donor animal conditional, and (ii) inserting the human transgene, which is a homolog of the target gene of the donor animal, into the physiologic locus of the target gene, at a site downstream from the target gene, in such a way that the native regulatory sequence for the target gene that are already in place will control expression of the human transgene when the target gene is knocked out. The transgene can be inserted without disrupting the host endogenous gene regulatory sequence or disturbing their function (i.e., not inactivating the regulatory sequence). The donor animal can be allowed to develop and live healthily, expressing its native protein encoded by the endogenous target gene until harvest of its organ, tissue or cells is needed, at which time the genetic switch is activated (e.g., by administering a drug) to knock out the target gene and switch to expression of the human transgene.

The sequence-specific insertion (knock-in) of one or more transgenes (e.g., recombinase recognition sites, recombinase, and/or a human transgene) into the genome of the donor species may be achieved by a sequence-specific endonuclease coupled with homologous recombination (HR) of the targeted chromosomal locus with the construct containing the transgene(s). Meyer et al., Proc. Natl. Acad. Sci. USA 107, 15022-15026 (2010). Cui et al., Nat. Biotechnol. 29(1), 64-67 (2010). Moehle et al., Proc Natl Acad Sci USA 104, 3055-3060 (2007). As the first step, the gene of a cell from the donor species is engineered in vitro. This process relies on targeting specific gene sequences with endonucleases that recognize and bind to such sequences and induce a double-strand break in the nucleic acid molecule. The double-strand break is then repaired by homologous recombination. If a template (e.g., a construct containing the transgene(s)) for homologous recombination is provided in trans, the double-strand break can be repaired using the provided template.

Non-limiting examples of the endonucleases include a zinc finger nuclease (ZFN), a ZFN dimer, a ZFNickase, a transcription activator-like effector nuclease (TALEN), or a RNA-guided DNA endonuclease (e.g., CRISPR/Cas9). Meganucleases are endonucleases characterized by their capacity to recognize and cut large DNA sequences (12 base pairs or greater). Any suitable meganuclease may be used to in the present methods to introduce transgenes to the donor animal's genome, such as endonucleases in the LAGLI-DADG family.

ZFNs can be composed of two or more (e.g., 2-8, 3-6, 6-8, or more) sequence-specific DNA binding domains (e.g., zinc finger domains) fused to an effector endonuclease domain (e.g., the FokI endonuclease). Porteus et al., Nat. Biotechnol. 23, 967-973 (2005). Kim et al. (2007) Hybrid restriction enzymes: Zinc finger fusions to Fok I cleavage domain, Proceedings of the National Academy of Sciences of USA, 93: 1156-1160. U.S. Pat. No. 6,824,978. PCT Publication Nos. WO1995/09233 and WO1994018313.

TALENs are composed of a TAL effector domain that binds to a specific nucleotide sequence and an endonuclease domain that catalyzes a double strand break at the target site (PCT Patent Publication No. WO2011072246; Miller et al., Nat. Biotechnol. 29, 143-148 (2011); Cermak et al., Nucleic Acid Res. 39, e82 (2011)). Sequence-specific endonucleases may be modular in nature, and DNA binding specificity is obtained by arranging one or more modules. Bibikova et al., Mol. Cell. Biol. 21, 289-297 (2001). Boch et al., Science 326, 1509-1512 (2009).

Another example of sequence-specific endonucleases includes RNA-guided DNA nucleases, e.g., the CRISPR/Cas system. The Cas9/CRISPR (Clustered Regularly-Interspaced Short Palindromic Repeats) system exploits RNA-guided DNA-binding and sequence-specific cleavage of target DNA. A guide RNA (gRNA) (e.g., containing 20 nucleotides) are complementary to a target genomic DNA sequence upstream of a genomic PAM (protospacer adjacent motifs) site (NNG) and a constant RNA scaffold region. The Cas (CRISPR-associated) 9 protein binds to the gRNA and the target DNA to which the gRNA binds and introduces a double-strand break in a defined location upstream of the PAM site. Geurts et al., Science 325, 433 (2009); Mashimo et al., PLoS ONE 5, e8870 (2010); Carbery et al., Genetics 186, 451-459 (2010); Tesson et al., Nat. Biotech. 29, 695-696 (2011). Wiedenheft et al. Nature 482,331-338 (2012); Jinek et al. Science 337,816-821 (2012); *Mali* et al. Science 339,823-826 (2013); Cong et al. Science 339,819-823 (2013).

The sequence-specific endonuclease of the methods and compositions described herein can be engineered, chimeric, or isolated from an organism. Endonucleases can be engineered to recognize a specific DNA sequence, by, e.g., mutagenesis. Seligman et al. (2002) Mutations altering the cleavage specificity of a homing endonuclease, Nucleic Acids Research 30: 3870-3879. Combinatorial assembly is a method where protein subunits form different enzymes can be associated or fused. Arnould et al. (2006) Engineering of large numbers of highly specific homing endonucleases that induce recombination to novel DNA targets, Journal of Molecular Biology 355: 443-458. In certain embodiments, these two approaches, mutagenesis and combinatorial assembly, can be combined to produce an engineered endonuclease with desired DNA recognition sequence.

The sequence-specific nuclease can be introduced into the cell in the form of a protein or in the form of a nucleic acid encoding the sequence-specific nuclease, such as an mRNA or a cDNA. Nucleic acids can be delivered as part of a larger construct, such as a plasmid or viral vector, or directly, e.g., by electroporation, lipid vesicles, viral transporters, microinjection, and biolistics. Similarly, the construct containing the one or more transgenes can be delivered by any method appropriate for introducing nucleic acids into a cell.

The present methods may also utilize recombinant adeno-associated virus (rAAV) mediated genome engineering. Kohli et al., Facile methods for generating human somatic cell gene knockouts using AAV, Nucleic Acids Res. January 2004; 32(1): e3. The single-stranded DNA rAAV viral vectors have high transduction rates and have a unique property of stimulating endogenous HR without causing double strand DNA breaks in the genome. A rAAV vector can be designed to any target genomic locus and perform gene alterations in mammalian cells. Konishi et al., Knock-in of Mutant K-ras in Nontumorigenic Human Epithelial Cells as a New Model for Studying K-ras-Mediated Transformation, Cancer Res., 2007, 67(18): 8460-7. Roock et al., Association of KRAS p. G13D mutation with outcome in patients with chemotherapy-refractory metastatic colorectal cancer treated with cetuximab, JAMA, October 2010, 304 (16): 1812-20.

In one embodiment, the desired changes to the donor animal genome are made in one step by using a nucleic acid cassette which contains both a conditionally knockout allele of the target gene followed downstream by the human transgene which is a homolog of the target gene (or followed downstream by a portion of the human transgene). The nucleic acid cassette is configured to have the target gene (or a portion of the target gene) flanked by recombinase recognition sites, with a stop codon before the second recombinase recognition site, followed by the corresponding human transgene (or a portion of the transgene) and a second stop codon. The nucleic acid cassette will direct the conditionally knockout allele of the target gene followed downstream by the human transgene (or a portion of the transgene) to be inserted into the native locus of the target gene. When knocked in, the human transgene (or a portion of the transgene) is located downstream of the first stop codon so that it is not expressed when the target gene is present.

In an exemplary embodiment, the transgene (e.g., an inducible Cre recombinase) is targeted to the ROSA26 locus to achieve ubiquitous transgene expression. Li et al., Dual Fluorescent Reporter Pig for Cre Recombination: Transgene Placement at the ROSA26 Locus. PLoS ONE, 2014, 9(7): e102455. In another embodiment, the transgene(s) is (are) targeted to the GGTA (GGTA1) locus so that alphaGal is disrupted at the same time. In a third embodiment, the transgene(s) is (are) targeted to the CMAH locus so that N-glycolylneuraminic acid (NeuGc) is disrupted at the same time. Wang et al., Erythrocytes from GGTA1/CMAH knockout pigs: implications for xenotransfusion and testing in non-human primates, Xenotransplantation, 2014, 21(4):376-384. In certain embodiments, the transgene(s) is (are) targeted to the locus of the gene encoding an enzyme producing other porcine antigen (e.g., the swine lymphocyte antigen (SLA) antigen, the blood group A/0 antigen, the Hanganutziu-Deicher (H-D) antigen, and/or etc.) so that the porcine antigen(s) is (are) disrupted at the same time. Magnusson et al., Release of pig leukocytes during pig kidney perfusion and characterization of pig lymphocyte carbohydrate xenoantigens, Xenotransplantation, 2003, 10(5):432-45.

The one or more transgene may be inserted into an exon or an intron.

In one embodiment, constructs containing one or more transgenes are used together with sequence-specific endonucleases to generate conditional knock-out alleles. For example, a method for generating a conditional knock-out allele for a target gene may contain the following steps: (1) introducing into the cell a construct containing one or more transgenes, wherein the construct comprises a 5' homology region, a 5' recombinase recognition site, a target gene sequence (which may contain at least one neutral mutation), a 3' recombinase recognition site, and a 3' homology region; and (2) introducing into the cell a sequence-specific nuclease that cleaves a sequence within the target gene of the cell genome, thereby producing a conditional knock-out allele in the cell. The target gene sequence in the construct and the endogenous target gene sequence may be identical except for the at least one neutral mutation. A neutral mutation means any mutation in the nucleotide sequence of the donor sequence that reduces homology between the mutated sequence and the target sequence but leaves the coding potential of the mutated sequence for a functional polypeptide intact. The neutral mutation decreases the number of undesired homologous recombination events, compared to a wild type sequence, between the construct and the target sequence that do not result in a conditional knock-out allele. In some embodiments, the neutral mutation also abrogates binding of the sequence-specific nuclease to the construct. Examples of neutral mutations include silent mutations, i.e., mutations that alter the nucleotide sequence but not the encoded polypeptide sequence. Neutral mutations also include conservative mutations, i.e., mutations that alter the nucleotide sequence and the encoded polypeptide sequence but that do not substantially alter the function of the resulting polypeptide. This is the case, for example, when one amino acid is substituted with another amino acid that has similar properties (size, charge, etc.). Because the mutations within the donor sequence are neutral, the donor sequence encodes a polypeptide that is functionally substantially similar to or indistinguishable from that encoded by the target sequence. The functionality of a peptide or protein can be assessed by methods well-known in the art, such as functional assays, enzymatic assays, and biochemical assays. The mutated sequence can replace the target sequence at its position in the target gene without substantially altering the functional properties of the polypeptide encoded by the target gene. However, once integrated in the target gene, subsequent removal of the donor sequence from the target gene can result in altered, reduced or loss of function of the polypeptide encoded by the target gene. U.S. Patent Publication No. 2015/0128300.

The 5' homology region is located 5' or "upstream" of the 5' recombinase recognition site and is homologous to a nucleic acid flanking the target gene sequence in its genomic context. Similarly, the 3' homology region is located 3' or "downstream" of the 3' recombinase recognition site and is homologous to a nucleic acid flanking the target gene sequence in its genomic context. The homology regions can be homologous to regions of the target gene and also, or instead, be homologous to regions upstream or downstream of the target gene. In one embodiment, the homology regions are homologous to chromosomal regions immediately adjacent to the target gene sequence. For example, in the case of the 5' homology region, the homology region is homologous to a sequence having its most 3' nucleotide immediately adjacent to the first (most 5') nucleotide of the target gene sequence. In one embodiment, homology regions are homologous to chromosomal regions that are not immediately adjacent to the target gene sequence on the chromosome. In some embodiments, the 5' and 3' homologous regions are each 90-100%, or 95-100% homologous to the cognate nucleic acid sequences flanking the target gene sequence in its genomic context.

The construct can further include certain sequences that provide structural or functional support, such as sequences of a plasmid or other vector that supports propagation of the donor construct (e.g., pUC19 vector). The construct can, optionally, also include certain selectable markers or reporters, some of which may be flanked by recombinase recognition sites for subsequent activation, inactivation, or deletion. The recombinase recognition sites flanking the optional marker or reporter can be the same or different from the recombinase recognition sites flanking the donor sequence.

Concomitant with, or sequential to, introduction of the donor construct, a sequence-specific endonuclease is introduced into the cell. The sequence-specific endonuclease recognizes and binds to a specific sequence within the target gene and introduces a double-strand break in the target gene. The donor sequence may be modified by at least one neutral mutation to reduce homologous recombination events that do not result in conditional knock-out alleles.

Any of the configurations described herein and contemplated for use in the invention can be introduced as a whole, or can be introduced in separate steps. For example, the LoxP sites can be introduced around the endogenous target gene (or a portion of the target gene) to be knocked out, along with a suitably placed stop codon in one or more separate steps, and then the transgene (or a portion of the transgene) added in a nucleic acid cassette in a separate step, or the construct can be created using a copy of the endogenous target gene (or a portion of the target gene) that is flanked by the recombinase recognition sites and added as a whole, in one step. Therefore, the natural gene can be used and expressed, or a copy or variant of the gene that has been flanked by the recombinase recognition sites can be inserted and expressed. Therefore, any of these methods can be used, so long as the resulting insertions to not interfere with the native regulatory sequence for the gene.

The modified DNA sequence to be introduced into the donor animal genome may be recombinant and produced in bacteria or another cell in culture, and also may be a variant of the endogenous target gene. Such variants may be at least 90% homologous to the native target gene and produce a translation product (a protein/polypeptide) that is able to act in the host animal system as (or substantially similar to) the native endogenous gene product acts. The variant may be 95%, 97%, 98%, 99%, 99.9% or 99.99% homologous to the native gene product (or a fragment thereof). Genes which encode the same protein as the native sequence but differ in the nucleic acid sequence due to the degeneracy of the code are contemplated as well.

In some embodiments, the methods described herein produce cells carrying heterozygous conditional knock-out alleles or homozygous conditional knock-out alleles, i.e., less than all or all of the endogenous alleles are replaced by the conditional knock-out allele.

In certain embodiments, the methods and compositions described herein can be used to target more than one genomic locus within a cell, i.e., for multiplex gene targeting. Insertion of multiple different corresponding transgenes in multiple different cassettes to be inserted into different corresponding host loci is also encompassed by the present method.

Methods for screening for the desired genotype are well known in the art and include PCR analysis, e.g., as described herein in the specific examples.

Cells of the donor species that may be used for the in vitro genetic engineering include, but are not limited to, fibroblasts, cumulus cells, precursor cells of adipocytes, undefined fetal gonad cells, cumulus cells, oviduct cells, skin cells, liver cells, macrophages, spleen cells, brain cells, and Sertoli cells. The cells can be of fetal, newborn and adult origin. The cells may be from a male or a female animal. In one embodiment, fetal-derived fibroblasts are used. In another embodiment, primordial germ cell-derived lines isolated from pig fetuses are used.

Any suitable cells that are developmentally competent, and possess a proliferative ability may be used for in vitro genetic engineering to produce genetically modified donor animals.

In one embodiment, somatic cells from the donor species are used; then nuclear transfer from somatic cells can introduce targeted gene alterations into the germ line. In another embodiment, induced pluripotent stem (iPS) cells from the donor species may be used. In certain embodiments, the cell is a somatic cell, a zygote or a pluripotent stem cell. The cell may be an embryonic stem (ES) cell.

The cell can be any eukaryotic cell, e.g., an isolated cell of an animal, such as a totipotent, pluripotent, or adult stem cell, a zygote, or a somatic cell. In certain embodiments, cells for use in the methods described herein are cells of non-human animals, such as domesticated animals (e.g., cows, sheep, cats, dogs, and horses), primates (e.g., non-human primates such as monkeys), rabbits.

Generation of Transgenic Donor Animals

Transgenes can be introduced into cells cultured in vitro, and cells containing the transgenes could be cultured and expanded. The expression level can be detected in individual cells, which could be determined by the addition of a reporter gene with a target gene. The cells with high level foreign gene expression would be selected to produce embryos which are prescreened for transgene integration prior to embryo transfer to surrogate mothers, to generate transgenic animals. U.S. Patent Publication No. 2016/0029604.

The transgenic animal may be produced by any suitable method known in the art, including, but not limited to, somatic cell nuclear transfer (SCNT), microinjection, embryonic stem (ES) cell manipulation, electroporation, cell gun, transfection, transduction, retroviral infection, etc.

Transgenic animals (e.g., swine) can be produced by introducing transgenes into the germline of the animal. Embryonal target cells at various developmental stages can be used to introduce the transgene construct. As is generally understood in the art, different methods are used to introduce the transgene depending on the stage of development of the embryonal target cell. One technique for transgenically altering an animal is to microinject a recombinant nucleic acid molecule into the male pronucleus of a fertilized egg so as to cause one or more copies of the recombinant nucleic acid molecule to be retained in the cells of the developing animal. Brinster et al. (1985) PNAS 82:4438-4442. The zygote may be used for micro-injection. The progeny of the transgenically manipulated embryos may be tested for the presence of the construct by, e.g., Southern blot analysis of a tissue. The stable integration of the transgene(s) into the genome of transgenic embryos allows permanent transgenic mammal lines carrying the recombinant nucleic acid molecule to be established.

Alternative methods for producing a mammal containing a transgene(s) include infection of fertilized eggs, embryo-derived stem cells, to potent embryonal carcinoma (EC) cells, or early cleavage embryos with viral expression vectors containing the recombinant nucleic acid molecule. (See for example, Palmiter et al. (1986) Ann. Rev. Genet. 20:465-499 and Capecchi (1989) Science 244:1288-1292)

Retroviral infection can also be used to introduce a transgene(s) into a cell. The developing embryo can be cultured in vitro to the blastocyst stage. During this time, the blastomeres can be targets for retroviral infection (Jaenich (1976) PNAS 73:1260-1264). Efficient infection of the blastomeres is obtained by enzymatic treatment to remove the zona pellucida (Hogan et al. (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner et al. (1985) PNAS 82:6927-6931; Van der Putten et al. (1985) PNAS 15 82:6148-6152). Transfection can be obtained by culturing the blastomeres on a monolayer of virus-producing cells (Van der Putten, supra; Stewart et al. (1987) EMBO J. 6:383-388). Alternatively, infection can be performed at a later stage. Virus or virus-producing cells can be injected into the blastocoele (Jahner et al. (1982) Nature 298:623.628). In addition, it is also possible to introduce transgenes into the germ line by intrauterine retroviral infection of the mid-gestation embryo (Jahner et al. (1982) supra).

Another approach, which may be useful in the construction of transgenic animals, would target transgene introduction into an embryonic stem cell (ES). ES cells are obtained from pre-implantation embryos cultured in vitro and fused with embryos (Evans et al. (1981) Nature 292:154-156; Bradley et al. (1984) Nature 309:255-258; Gossler et al. (1986) PNAS 83:9065-9069; and Robertson et al. (1986) Nature 322:445-448). Transgenes might be efficiently introduced into the ES cells by DNA transfection or by retrovirus-mediated transduction. Such transformed ES cells could thereafter be combined with blastocysts, e.g., from a swine. The ES cells could be used thereafter to colonize the embryo and contribute to the germ line of the resulting chimeric animal. Jaenisch (1988) Science 240:1468-1474.

Introduction of the transgene sequence at the fertilized oocyte stage or at a later embryonic stage may be employed.

In certain embodiments, the transgenic swine of the present invention is produced by: i) microinjecting a recombinant nucleic acid molecule comprising the transgene(s) into a fertilized swine egg to produce a genetically altered swine egg; ii) implanting the genetically altered swine egg into a host female swine; iii) maintaining the host female for a time period equal to a substantial portion of the gestation period of said swine fetus, iv) harvesting a transgenic swine having at least one swine cell that has developed from the genetically altered mammalian egg, which expresses the transgene(s).

In general, the use of microinjection protocols in transgenic animal production may be divided into several phases: (a) preparation of the animals; (b) recovery and maintenance in vitro of one or two-celled embryos; (c) microinjection of the embryos; and (d) re-implantation of embryos into recipient females. The methods used for producing transgenic livestock, particularly swine, may or may not differ in principle from those used to produce transgenic mice. Gordon et al. (1983) Methods in Enzymology 101:411. Gordon et al. (1980) PNAS 77:7380. Hammer et al. (1985) Nature 315:680. Hammer et al. (1986) J. Anim. Sci. 63:269-278. Wall et al. (1985) Biol Reprod. 32:645-651. Pursel et al. (1989) Science 244:1281-1288. Vize et al. (1988) J Cell Science 90:295-300. Muller et al. (1992) Gene 121:263-270, and Velander et al (1992) PNAS 89:12003-12007. PCT Publication WO 90/03432. PCT Publication WO 92/22646 and references cited therein.

One step of the preparatory phase may involve synchronizing the estrus cycle of at least the donor females, and inducing superovulation in the donor females prior to mating. Superovulation typically involves administering drugs at an appropriate stage of the estrus cycle to stimulate follicular development, followed by treatment with drugs to synchronize estrus and initiate ovulation. Pregnant mare's serum may be used to mimic the follicle-stimulating hormone (FSH) in combination with human chorionic gonadotropin (hCG) to mimic luteinizing hormone (LH). Wall et al. (1985) Biol. Reprod. 32:645 describing superovulation of pigs.

After mating, one or two-cell fertilized eggs from the superovulated females are harvested for microinjection. A variety of protocols useful in collecting eggs from pigs are known. For example, in one approach, oviducts of fertilized superovulated females can be surgically removed and isolated in a buffer solution/culture medium, and fertilized eggs expressed from the isolated oviductal tissues. See, Gordon et al. (1980) PNAS 77:7380; and Gordon et al. (1983) Methods in Enzymology 101:411. Alternatively, the oviducts can be cannulated and the fertilized eggs can be surgically collected from anesthetized animals by flushing with buffer solution/culture medium, thereby eliminating the need to sacrifice the animal. See Hammer et al. (1985) Nature 315:600.

The timing of the embryo harvest after mating of the superovulated females can depend on the length of the fertilization process and the time required for adequate enlargement of the pronuclei. Fertilized eggs appropriate for microinjection, such as one-cell ova containing pronuclei, or two-cell embryos, can be readily identified under a dissecting microscope. Gordon et al. (1983) Methods in Enzymology 101:411; and Gordon et al. (1980) PNAS 77:7380. Wall et al. (1985) Biol. Reprod. 32:645. Molecular Cloning: A Laboratory Manual, Second Edition. Maniatis et al. eds., Cold Spring Harbor, N.Y. (1989).

The recombinant nucleic acid molecule may be microinjected into the swine egg to produce a genetically altered mammalian egg using known techniques. The nucleic acid molecule may be microinjected directly into the pronuclei of the fertilized eggs. Gordon et al. (1980) PNAS 77:7380-7384. Brinster et al. (1985) PNAS 82:4438-4442. Hammer et al. (1985) Nature 315:600-603.

Cells which survive the microinjection are subsequently used for implantation in a host female. The genetically altered mammalian embryo is then transferred to the oviduct or uterine horns of the recipient. See, for example, Gordon et al. (1983) Methods in Enzymology 101:411; Gordon et al. (1980) PNAS 77:7390; Hammer et al. (1985) Nature 315: 600; and Wall et al. (1985) Biol. Reprod. 32:645. The host female mammals containing the implanted genetically altered mammalian eggs are maintained for a sufficient time period to give birth to a transgenic mammal having at least one cell which expresses the recombinant nucleic acid molecule comprising the transgene(s) that has developed from the genetically altered mammalian egg.

For additional methods for producing transgenic swine, see Martin et al. Production of transgenic swine, Transgenic Animal Technology: A Laboratory Handbook, Carl A. Pinkert, ed., Academic Press; 315-388. 1994; U.S. Pat. No. 5,523,226; and U.S. Pat. No. 6,498,285.

In an embodiment, the transgenic animals of the invention are made by somatic cell nuclear transfer (SCNT).

Construction of Nuclear Transfer Embryos

Transgenic donor animals may be produced through genomic modification of somatic cells in vitro followed by somatic cell nuclear transfer (SCNT). In this process, the nuclei of somatic cells are transferred into enucleated oocytes (e.g., metaphase II oocytes), and then this complex is activated. Reconstructed embryos are then cultured and transferred to synchronized recipients for gestation.

In nuclear transfer (NT), oocytes may be enucleated by a chemical compound such as bisbenzimide. Enucleation of oocytes can be also performed by aspirating the first polar body and adjacent cytoplasm without staining the chromatin ("blind enucleation").

Any suitable approach may be used to transfer the donor nuclei. In one embodiment, the donor cell is directly injected into an enucleated oocyte. In another embodiment, the donor cell is injected into the perivitelline space and subsequently fused with the recipient oocyte by electrical pulses. Lai et al., Creating genetically modified pigs by using nuclear transfer, Reproductive Biology and Endocrinology 2003, 1:82.

After the donor nuclei are transferred into the enucleated oocytes, the reconstructed embryos are activated to initiate subsequent development. Activation of oocytes can be induced artificially by a variety of physical and chemical agents, such as electrical activation, electrofusion, or activation by ionophore followed by 6-dimethylaminourine, combined thimerosal/DTT treatment.

Embryo Transfer

To minimize any adverse effect of the in vitro conditions on the development of the embryos, transfer to the surrogate is generally at a very early stage. A number of the NT embryos may be transferred into a single surrogate. In the pig, pregnancy recognition by the surrogate requires a signal from four or more embryos around day 12 of gestation. Lai et al., Creating genetically modified pigs by using nuclear transfer, Reproductive Biology and Endocrinology 2003, 1:82. If not enough NT embryos are available for transfer, then the following strategies may be employed. One strategy is to co-transfer "helper embryos" as an aid to inducing and maintaining pregnancy. These "helper embryos" maybe parthenogenetic embryos that are capable of establishing a pregnancy but degenerate by day 30 of gestation because of genomic imprinting. Alternatively, the helper embryos might be derived from a normal mating. Finally, administration of estradiol, the normal signal for maternal recognition of pregnancy, on day 12 can maintain the pregnancy of small litters.

Target Genes/Transgenes

The methods are envisioned for use with one gene, or with multiple genes in multiple locations of the donor (host) animal.

Proteins/polypeptides encoded by the target genes/transgene (or a portion of the target gene, or a portion of the transgene) may include a cytokine, a cytokine receptor, a cell adhesion molecule, complement regulatory protein, an anti-coagulant, an anti-platelet, an immunosuppressive, growth hormones and their receptors, or combinations thereof. Non-limiting examples of proteins encoded by the target genes (or the transgene) include IL-3, IL-3R; CD47, SIRP-α; GM-CSF, GM-CSF receptor, c-kit, stem cell factor (SCF, c-kit ligand), interleukin-4, interleukin-4 receptor, thrombopoietin, thrombopoietin receptor (mpl, CD110), erythropoietin, erythropoietin receptor, renin, VLA-5 (alpha-5 integrin and beta1 integrin), fibronectin, angiotensin, thrombomodulin (TBM), DAF, CD39, PDL-1, PDL-2, PD1, LDL-LDL receptor; HDL-HDL receptor; HGF, HGF receptor; CD200; ligands for paired Ig-like receptor (PIR)-B; ligands for immunoglobulin-like transcript (ILT)3; and ligands for CD33-related receptors.

The present transgenic donor animals may comprise a conditional knockout allele of the target gene, or a conditional knockout allele of a fragment of the target gene. Similarly, the present transgenic donor animals may comprise a protein or polypeptide encoded by the target gene, or a polypeptide or a peptide encoded by a fragment of the target gene (i.e., the polypeptide or peptide is a fragment of the protein or polypeptide encoded by the wildtype allele of the target gene).

The conditional knockout allele of the target gene may comprise a nucleic acid sequence at least 70%, at least 75%, at least 80%, at least 85%, at least 90%, at least 95%, at least 96%, at least 97%, at least 98%, at least 99%, about 70%, about 75%, about 80%, about 85%, about 90%, about 95%, about 96%, about 97%, about 98%, about 99%, or (about) 100% identical to the sequence of the wildtype allele of the target gene or a fragment of the wildtype allele of the target gene of the first mammalian species.

The protein or polypeptide encoded by the conditional knockout allele of the target gene may comprise an amino acid sequence at least 70%, at least 75%, at least 80%, at least 85%, at least 90%, at least 95%, at least 96%, at least 97%, at least 98%, at least 99%, about 70%, about 75%, about 80%, about 85%, about 90%, about 95%, about 96%, about 97%, about 98%, about 99%, or (about) 100%, identical to the sequence of the wildtype protein or polypeptide encoded by the wildtype allele of the target gene, or identical to the sequence of a fragment of the wildtype protein or polypeptide encoded by the wildtype allele of the target gene of the first mammalian species.

With respect to the transgene, the present transgenic donor animals may comprise a transgene, or a fragment of the transgene. Similarly, the present transgenic donor animals may comprise a protein encoded by a transgene, or a polypeptide or a peptide encoded by a fragment of the transgene (i.e., the polypeptide or peptide is a fragment of the protein or polypeptide encoded by the transgene).

The transgene may comprise a nucleic acid sequence at least 70%, at least 75%, at least 80%, at least 85%, at least 90%, at least 95%, at least 96%, at least 97%, at least 98%, at least 99%, about 70%, about 75%, about 80%, about 85%, about 90%, about 95%, about 96%, about 97%, about 98%, about 99%, or (about) 100% identical to the sequence of the wildtype allele of the transgene or a fragment of the wildtype allele of the transgene of the second mammalian species.

The protein or polypeptide encoded by the transgene may comprise an amino acid sequence at least 70%, at least 75%, at least 80%, at least 85%, at least 90%, at least 95%, at least 96%, at least 97%, at least 98%, at least 99%, about 70%, about 75%, about 80%, about 85%, about 90%, about 95%, about 96%, about 97%, about 98%, about 99%, or (about) 100% identical to the sequence of the wildtype protein or polypeptide encoded by the wildtype allele of the transgene, or identical to the sequence of a fragment of the wildtype protein or polypeptide encoded by the wildtype transgene of the second mammalian species.

Useful fragments and variants include those which retain the ability to bind with the appropriate receptor on an immune cell (e.g., a fragment which binds to and activities the normal receptor) and mediates at least one biological activity of the molecule. For example, a cell of a first species (e.g., swine) which expresses a polypeptide including the fragment or variant is less susceptible to phagocytosis by a phagocytic cell (e.g., a macrophage) of a second species, as compared to a control (e.g., a cell which does not express the fragment or variant). The polypeptides may be fusion proteins and may be membrane-associated or soluble forms.

Some additional examples of transgenes (or target genes) that may be expressed (or conditionally knocked out) are in Table 1. The receptor of each of the molecules of Table 1 is also encompassed by the present application.

TABLE 1

Human cytokines and their receptors for use in embodiments of the invention[1]

| Name | Synonym(s) | Amino Acids | Chromosome | Molecular Weight[2] | Cytokine Receptor(s)(D) and Form | Receptor Location(s) |
|---|---|---|---|---|---|---|
| Interleukins | | | | | | |
| IL-1-like | | | | | | |
| IL-1α | hematopoietin-1 | 271 | 2q14 | 30606 | CD121a, CDw121b | 2q12, 2q12-q22 |
| IL-1β | catabolin | 269 | 2q14 | 20747 | CD121a, CDw121b | 2q12, 2q12-q22 |
| IL-1RA | IL-1 receptor antagonist | 177 | 2q14.2 | 20055 | CD121a | 2q12 |
| IL-18 | interferon-γ inducing factor | 193 | 11q22.2-q22.3 | 22326 | IL-18Rα, β | 2q12 |
| Common g chain (CD132) | | | | | | |
| IL-2 | T cell growth factor | 153 | 4q26-q27 | 17628 | CD25, 122, 132 | 10p15-p14, 22q13.1, Xq13.1 |
| IL-4 | BSF-1 | 153 | 5q31.1 | 17492 | CD124, 213a13, 132 | 16p11.2-12.1, X, Xq13.1 |
| IL-7 | | 177 | 8q12-q13 | 20186 | CD127, 132 | 5p13, Xq13.1 |
| IL-9 | T cell growth factor P40 | 144 | 5q31.1 | 15909 | IL-9R, CD132 | Xq28 or Yq12, Xq13.1 |
| IL-13 | P600 | 132 | 5q31.1 | 14319 | CD213a1, 213a2, CD1243, 132 | X, Xq13.1-q28, 16p11.2-12.1, Xq13.1 |

TABLE 1-continued

Human cytokines and their receptors for use in embodiments of the invention[1]

| Name | Synonym(s) | Amino Acids | Chromosome | Molecular Weight[2] | Cytokine Receptor(s)(D) and Form | Receptor Location(s) |
|---|---|---|---|---|---|---|
| IL-15 | | 162 | 4q31 | 18086 | IL-15Ra, CD122, 132 | 10p14-p14, 22q13.1, Xq13.1 |
| Common b chain (CD131) | | | | | | |
| IL-3 | multipotential CSF, MCGF | 152 | 5q31.1 | 17233 | CD123, CDw131 | Xp22.3 or Yp11.3, 22q13.1 |
| IL-5 | BCDF-1 | 134 | 5q31.1 | 15238, homodimer | CDw125, 131 | 3p26-p24, 22q13.1 |
| Also related | | | | | | |
| GM-CSF | CSF-2 | 144 | 5q31.1 | 16295 | CD116, CDw131 | Xp22.32 or Yp11.2, 22q13.1 |
| IL-6-like | | | | | | |
| IL-6 | IFN-β2, BSF-2 | 212 | 7p21 | 23718 | CD126, 130 | 1q21, 5q11 |
| IL-11 | AGIF | 199 | 19q13.3-13.4 | 21429 | IL-11Ra, CD130 | 9p13, 5q11 |
| Also related | | | | | | |
| G-CSF | CSF-3 | 207 | 17q11.2-q12 | 21781 | CD114 | 1p35-p34.3 |
| IL-12 | NK cell stimulatory factor | 219/328 | 3p12-p13.2/ 5q31.1-q33.1 | 24844/37169 heterodimer | CD212 | 19p13.1, 1p31.2 |
| LIF | leukemia inhibitory factor | 202 | 22q12.1-q12.2 | 22008 | LIFR, CD130 | 5p13-p12 |
| OSM | oncostatin M | 252 | 22q12.1-q12.2 | 28484 | OSMR, CD130 | 5p15.2-5p12 |
| IL-10-like | | | | | | |
| IL-10 | CSIF | 178 | 1q31-q32 | 20517, homodimer | CDw210 | 11q23 |
| IL-20 | | 176 | 2q32.2 | 20437 | IL-20Ra, β | ? |
| Others | | | | | | |
| IL-14 | HMW-BCGF | 498 | 1 | 54759 | IL-14R | ? |
| IL-16 | LCF | 631 | 15q24 | 66694, homotetramer | CD4 | 12pter-p12 |
| IL-17 | CTLA-8 | 155 | 2q31 | 17504, homodimer | CDw217 | 22q11.1 |
| Interferons | | | | | | |
| IFN-α | | 189 | 9p22 | 21781 | CD118 | 21q22.11 |
| IFN-β | | 187 | 9p21 | 22294 | CD118 | 21q22.11 |
| IFN-γ | | 166 | 12q14 | 19348, homodimer | CDw119 | 6q23-q24 |
| TNF | | | | | | |
| CD154 | CD40L, TRAP | 261 | Xq26 | 29273, homotrimer | CD40 | 20q12-q13.2 |
| LT-β | | 244 | 6p21.3 | 25390, heterotrimer | LTβR | 12p13 |
| TNF-α | cachectin | 233 | 6p21.3 | 25644, homotrimer | CD120a, b | 12p13.2, 1p36.3-p36.2 |
| TNF-β | LT-α | 205 | 6p21.3 | 22297, heterotrimer | CD120a, b | 12p13.2, 1p36.3-p36.2 |
| 4-1BBL | | 254 | 19p13.3 | 26624, trimer? | CDw137 (4-1BB) | 1p36 |
| APRIL | TALL-2 | 250 | 17p13.1 | 27433, trimer? | BCMA, TACI | 16p13.1, 17p11.2 |
| CD70 | CD27L | 193 | 19p13 | 21146, trimer? | CD27 | 12p13 |
| CD153 | CD30L | 234 | 9q33 | 26017, trimer? | CD30 | 1p36 |
| CD178 | FasL | 281 | 1q23 | 31485, trimer? | CD95 (Fas) | 10q24.1 |
| GITRL | | 177 | 1q23 | 20307, trimer? | GITR | 1p36.3 |

TABLE 1-continued

Human cytokines and their receptors for use in embodiments of the invention[1]

| Name | Synonym(s) | Amino Acids | Chromosome | Molecular Weight[2] | Cytokine Receptor(s)(D) and Form | Receptor Location(s) |
|---|---|---|---|---|---|---|
| LIGHT | | 240 | 16p11.2 | 26351, trimer? | LTbR, HVEM | 12p13, 1p36.3-p36.2 |
| OX40L | | 183 | 1q25 | 21050, trimer? | OX40 | 1p36 |
| TALL-1 | | 285 | 13q32-q34 | 31222, trimer? | BCMA, TACI | 16p13.1, 17p11.2 |
| TRAIL | Apo2L | 281 | 3q26 | 32509, trimer? | TRAILR1-4 | 8p21 |
| TWEAK | Apo3L | 249 | 17p13 3 | 27216, trimer? | Apo3 | 1p36.2 |
| TRANCE | OPGL | 317 | 13q14 | 35478, trimer? | RANK, OPG | 18q22.1, 8q24 |
| TGF-β | | | | | | |
| TGF-β1 | TGF-β | 390 | 19q13.1 | 44341, homodimer | TGF-βR1 | 9q22 |
| TGF-β2 | | 414 | 1q41 | 47747, homodimer | TGF-βR2 | 3p22 |
| TGF-β3 | | 412 | 14q24 | 47328, homodimer | TGF-βR3 | 1p33-p32 |
| Miscellaneous hematopoietins | | | | | | |
| Epo | erythropoietin | 193 | 7q21 | 21306 | EpoR | 19p13.3-p13.2 |
| Tpo | MGDF | 353 | 3q26.3-q27 | 37822 | TpoR | 1p34 |
| Flt-3L | | 235 | 19q13.1 | 26416 | Flt-3 | 13q12 |
| SCF | stem cell factor, c-kit ligand | 273 | 12q22 | 30898, homodimer | CD117 | 4q11-q12 |
| M-CSF | CSF-1 | 554 | 1p21-p13 | 60119, homodimer | CD115 | 5q33-q35 |
| MSP | Macrophage stimulating factor, MST-1 | 711 | 3p21 | 80379 | CDw136 | 3p21.3 |

[1]List assembled using data from Gene Cards.
[2]Data describes the unprocessed precursor.
[3]Can be found in complexes.

IL-3 and IL-3 Receptor

Interleukin-3 (IL-3) acts by binding to the interleukin-3 receptor. IL-3 stimulates the differentiation of multipotent hematopoietic stem cells into myeloid progenitor cells or, with the addition of IL-7, into lymphoid progenitor cells. In addition, IL-3 stimulates proliferation of all cells in the myeloid lineage (granulocytes, monocytes, and dendritic cells), in conjunction with other cytokines, e.g., erythropoietin (EPO), granulocyte macrophage colony-stimulating factor (GM-CSF), stem cell factor, FLT3-ligand, thrombopoietin (which acts on early hematopoietic progenitors; Vainchenker et al., Thrombosis and Haemostasis, 1995, 74:526) and IL-6. IL-3 may be secreted by stromal cells, basophils and activated T cells, etc. The human IL-3 may have 152 amino acid residues. IL-3 may be glycosylated.

T lymphocytes are the major cellular source of IL-3, although lesser amounts may be produced by natural killer cells, mast cells, thymic epithelium, and possibly some marrow stromal cells. Two recent clinical observations suggest an important role for IL-3 in vivo. First, infusions of recombinant IL-3 in humans or primates with bone marrow (BM) failure following transplantation stimulate production of red blood cells (RBCs), white blood cells (WBCs) and platelets, confirming its multilineage action. Second, removal of T lymphocytes from donor marrow may frequently result in graft failure in the allogeneic BM transplant recipient. Kenneth et al., Blood, Vol81, No 7 (April 1). 1993: pp 1915-1922; Serum Interleukin-3 Levels Following Autologous or Allogeneic Bone Marrow Transplantation: Effects of T-cell depletion, Blood Stem Cell Infusion, and Hematopoietic Growth Factor Treatment.

The genes for IL-3, IL-5 and GM-CSF are closely linked and lie on human chromosome 5 and mouse chromosome 11. IL-3, originally termed multicolony stimulating factor (multi-CSF), is produced by activated T cells and stimulates both multipotential hematopoietic cells (stem cells) and developmentally committed cells such as granulocytes, macrophages, mast cells, erythroid cells, eosinophils, basophils and megakaryocytes. The human IL-3 receptor consists of CD123 and βc/CDw131. The mouse IL-3 receptor has an additional β chain called $β_{IL-3}$, the function of which can be compensated for by CD123 if knocked out. Knocking out CD123 itself has little effect on hematopoiesis. On the other hand, if IL-3 is knocked out, mast cell and basophil development upon challenge is affected, as well as some forms of DTH, confirming a role for IL-3 in host defense and expanding hematopoietic effector cells.

Thrombomodulin (TBM)

The inability of porcine thrombomodulin (TM) to activate human anticoagulant protein C after pig-to-human xenotransplantation may lead to an aberrant activation of coagulation with microthrombosis and ultimately failure of the transplanted organ. Petersen et al, Xenotransplantation. 2009 November-December; 16(6):486-95.

Thrombomodulin (TBM) is an important vascular anticoagulant that has species specific effects. Although human TBM chimeric mice are viable and are not subject to spontaneous hemorrhage, they have a prolonged bleeding time. Crikis et al, Anti-inflammatory and anticoagulant effects of transgenic expression of human thrombomodulin in mice, Am. J. Transplant. 2010 February; 10(2):242-50.

Newly derived swine at National Swine Resource and Research Center (NSRRC, RADIL, University Missouri, Columbia Mo.) have been developed on the GalT-KO that have co-segregating (human decay-accelerating factor) hDAF (human DAF) insertions (i.e. homozygous animals will have two copies of hDAF knocked in). The successful addition of human transgenes into the same loci has been accomplished using this same construct and have demonstrated effective expression of CD39 in developed swine. In preliminary experimentation, cardiac vascularized xenografts and islet xenotransplants also have been studied using these cloned transgenic swine as organ and cell donors.

CD39

CD39, a vascular nucleoside triphosphate diphosphohydrolase (NTPDase), converts ATP and ADP to AMP, which is further degraded to the antithrombotic and anti-inflammatory mediator adenosine. hCD39 (human CD39) transgenic mice exhibited impaired platelet aggregation, prolonged bleeding times, and resistance to systemic thromboembolism. Moreover, these thromboregulatory manifestations in hCD39 transgenic mice suggest important therapeutic potential in clinical vascular disease and in the control of serious thrombotic events that compromise the survival of porcine xenografts in primates. Dwyer et al., J. Clin. Invest. 2004 May; 113(10): 1440-6. Overexpression of CD39/nucleoside triphosphate diphosphohydrolase-1 also is reported to decrease smooth muscle cell proliferation and prevent neointima formation after angioplasty. Koziak et al., J Thromb Haemost. 2008 July; 6(7):1191-7.

Liver grafts from CD39-overexpressing rodents are protected from ischemia reperfusion injury due to reduced numbers of resident CD4+ T cells. However, hCD39 transgenic mice have associated thromboregulatory problems. CD39 modulates hematopoietic stem cell recruitment and promotes liver regeneration in mice and humans after partial hepatectomy. Schmelzle et al., Ann. Surg. 2013 April; 257 (4):693-701; Pommey et al., Hepatology, 2013 April; 57(4): 1597-606, Suppressing hCD39 expression in transgenic hosts until a short time prior to harvesting transgenic cells, organs or tissue would reduce adverse side effects associated with the overexpression.

Immune-Inhibitory Molecules

CD47

CD47, also known as integrin-associated protein (IAP), is a ubiquitously expressed 50-kDa cell surface glycoprotein and serves as a ligand for signal regulatory protein (SIRP)α (also known as CD172a, and SHPS-1). Brown, Curr. Opin. Cell. Biol., 14(5):603-7, 2002; Brown and Frazier, Trends Cell Biol., 111(3):130-5, 2001. CD47 and SIRPα constitute a cell-cell communication system that plays important roles in a variety of cellular processes including cell migration, adhesion of B cells, and T cell activation (Liu et al., J. Biol. Chem. 277:10028, 2002; Motegi et al., EMBO 122:2634, 2003; Yoshida et al., J. Immunol. 168:3213, 2002; Latour et al., J. Immunol. 167:2547, 2001). In addition, the CD47-SIRPa system is implicated in negative regulation of phagocytosis by macrophages. CD47 on the surface of some cell types (i.e., erythrocytes, platelets or leukocytes) inhibited phagocytosis by macrophages. The role of CD47/SIRPa interaction in the inhibition of phagocytosis has been illustrated by the observation that primary, wild-type mouse macrophages rapidly phagocytose unopsonized red blood cells (RBCs) obtained from CD47-deficient mice but not those from wild-type mice (Oldenborg et al., Science 288: 2051, 2000). It has also been reported that through its receptors, SIRPa, CD47 inhibits both Fcγ and complement receptor mediated phagocytosis (Oldenborg et al., J. Exp. Med. 193:855, 2001). Polypeptides which include all or a portion of the extracellular domain of CD47 are contemplated. See, e.g., Motegi et al., EMBO J., 22(11): 2634-2644, 2003, which describes the construction of a human CD47-Fc fusion protein.

Amino acid sequences of human CD47 can be found under the following NCBI Reference Sequence (RefSeq) accession numbers: NP_001768; NP_942088; and NP_001020250. Nucleic acid sequences encoding human CD47 can be found under the following NCBI RefSeq accession numbers: NM_001777; NM_198793; and NM_001025079. Sequences of CD47 in other species are also known. See, for example, the amino acid sequences under the following NCBI RefSeq numbers: XP_516636 (chimpanzee); XP_535729 (dog); NP_034711 (mouse); NP_062068 (rat); and XP_416623 (chicken).

Other immune-inhibitory molecules suitable for the methods and compositions described herein are those which interact inefficiently, or fail to interact, with counterpart ligands which is derived from another species (i.e., the ligands have low cross-reactivity across species barriers). Exemplary immune-inhibitory molecules include CD200, ligands for paired Ig-like receptor (PIR)-B, ligands for immunoglobulin-like transcript (ILT)3, and ligands for CD33-related receptors. CD200 is a type-1 membrane glycoprotein and is a member of the immunoglobulin (Ig) superfamily. Sequences for human CD200 can be found under NCBI RefSeq accession numbers NP_005935 and NP_001004196. ILT3 is also a member of the Ig superfamily. The cloning of a human ILT3 sequence is described in Cella et al., J. Exp. Med., 185(10):1743-1751, 1997. CD33-related receptors are discussed in Crocker and Varki, 1: Trends Immunol., 22(6):337-42, 2001.

Other Genetic Modifications of the Donor Animal

The donor animal may also have other genetic modifications including, but not limited to, deficiency in expression of a carbohydrate modifying enzyme (e.g., α-1,3-galactosyltransferase) by knocking out the GGTA gene, and/or expression of a carbohydrate modifying enzyme, such as an α-Galactosidase A (αGalA) enzyme. U.S. Patent Publication No. 2015/0017130. U.S. Pat. No. 6,849,448. WO 2004016742. In one embodiment, the endogenous GGTA gene in the donor animal can be conditionally knocked out using the Cre-lox system shortly before cells, organs or tissues are harvested from the donor animal for transplantation.

The transgenic cells, organs, tissues, and animals described herein can include additional genetic modifications, such as modifications that render the cells and organs more suitable for xenotransplantation. Transgenic swine expressing inhibitors of complement are described, e.g., in U.S. Pat. No. 6,825,395. Compositions for depleting xenoreactive antibodies are described in U.S. Pat. No. 6,943,239. In some embodiments, the transgenic cells, organs, and animals further include transgenic nucleic acid molecules that direct the expression of enzymes, capable of modifying, either directly or indirectly, cell surface carbohydrate epitopes such that the carbohydrate epitopes are no longer recognized by natural antibodies in a transplantation recipient (e.g., a human) or by the cell-mediated immune response of the host, thereby reducing the immune system response elicited by the presence of such carbohydrate epitopes. In various embodiments, the transgenic cells, organs and animals (e.g., non-human mammals such as swine) express nucleic acid molecules encoding functional recombinant a-Galactosidase A (aGalA) enzyme which modifies the carbohydrate epitope Gala(1,3)Gal. U.S. Pat. No. 6,455,037.

In various embodiments, the transgenic cells, organs, and animals described herein are deficient for expression of a carbohydrate-modifying enzyme, such that the cells, etc., are rendered less reactive to antibodies (e.g., natural antibodies) present in a xenogeneic host. Expression can be rendered deficient by inactivating a gene expressing the enzyme in an organism (e.g., using gene knockout technology, or by other methods such as RNA interference). Swine deficient for expression of one such carbohydrate modifying enzyme, α-1,3 galactosyltransferase, are described, e.g., in U.S. Pat. No. 6,849,448.

Transplantation

Cells, tissues, organs or body fluids of the present transgenic donor animal may be used for transplantation (e.g., xenotransplantation). The graft harvested from the donor animal for transplantation may include, but are not limited to, a heart, a kidney, a liver, a pancreas, a lung transplant, an intestine, skin, thyroid, bone marrow, small bowel, a trachea, a cornea, a limb, a bone, an endocrine gland, blood vessels, connective tissue, progenitor stem cells, blood cells, hematopoietic cells, Islets of Langerhans, brain cells and cells from endocrine and other organs, bodily fluids, and combinations thereof.

The cell can be any type of cell. In certain embodiments, the cell is a hematopoietic cell (e.g., a hematopoietic stem cell, lymphocyte, a myeloid cell), a pancreatic cell (e.g., a beta-islet cell), a kidney cell, a heart cell, or a liver cell.

Bone marrow cells (BMC), or hematopoietic stem cells (e.g., a fetal liver suspension or mobilized peripheral blood stem cells) of the donor animal can be injected into the recipient.

The method can include administering one or more treatments, e.g., a treatment which inhibits T cells, blocks complement, or otherwise down regulates the recipient immune response to the graft.

Treatments that promote tolerance and/or decrease immune recognition of the graft include use of immunosuppressive agents (e.g., cyclosporine, FK506), antibodies (e.g., anti-T cell antibodies such as polyclonal anti-thymocyte antisera (ATG), and/or a monoclonal anti-human T cell antibody, such as LoCD2b), irradiation, and methods to induce mixed chimerism. U.S. Pat. Nos. 6,911,220; 6,306, 651; 6,412,492; 6,514,513; 6,558,663; and U.S. Pat. No. 6,296,846. Kuwaki et al., Nature Med., 11(1):29-31, 2005. Yamada et al., Nature Med. 11 (1):32-34, 2005.

In some embodiments, the recipient is thymectomized and/or splenectomized. Thymic irradiation can be used.

In some embodiments, the recipient is administered low dose radiation (e.g., a sublethal dose of between 100 rads and 400 rads whole body radiation). Local thymic radiation may also be used.

The recipient can be treated with an agent that depletes complement, such as cobra venom factor.

Natural antibodies can be eliminated by organ perfusion, and/or transplantation of tolerance-inducing bone marrow. Natural antibodies can be absorbed from the recipient's blood by hemoperfusion of a liver of the donor species. The cells, tissues, or organs used for transplantation may be genetically modified such that they are not recognized by natural antibodies of the host (e.g., the cells are a-1,3-galactosyltransferase deficient).

In some embodiments, the methods include treatment with a human anti-human CD154 mAb, mycophenolate mofetil, and/or methylprednisolone. The methods can also include agents useful for supportive therapy such as anti-inflammatory agents (e.g., prostacyclin, dopamine, ganiclovir, levofloxacin, cimetidine, heparin, antithrombin, erythropoietin, and aspirin).

In some embodiments, donor stromal tissue is administered.

An immunosuppressant, also referred to as an immunosuppressive agent, can be any compound that decreases the function or activity of one or more aspects of the immune system, such as a component of the humoral or cellular immune system or the complement system.

Non-limiting examples of immunosuppressants include, (1) antimetabolites, such as purine synthesis inhibitors (such as inosine monophosphate dehydrogenase (IMPDH) inhibitors, e.g., azathioprine, mycophenolate, and mycophenolate mofetil), pyrimidine synthesis inhibitors (e.g., leflunomide and teriflunomide), and antifolates (e.g., methotrexate); (2) calcineurin inhibitors, such as tacrolimus, cyclosporine A, pimecrolimus, and voclosporin; (3) TNF-alpha inhibitors, such as thalidomide and lenalidomide; (4) IL-1 receptor antagonists, such as anakinra; (5) mammalian target of rapamycin (mTOR) inhibitors, such as rapamycin (sirolimus), deforolimus, everolimus, temsirolimus, zotarolimus, and biolimus A9; (6) corticosteroids, such as prednisone; and (7) antibodies to any one of a number of cellular or serum targets (including anti-lymphocyte globulin and anti-thymocyte globulin).

Non-limiting exemplary cellular targets and their respective inhibitor compounds include, but are not limited to, complement component 5 (e.g., eculizumab); tumor necrosis factors (TNFs) (e.g., infliximab, adalimumab, certolizumab pegol, afelimomab and golimumab); IL-5 (e.g., mepolizumab); IgE (e.g., omalizumab); BAYX (e.g., nerelimomab); interferon (e.g., faralimomab); IL-6 (e.g., elsilimomab); IL-12 and IL-13 (e.g., lebrikizumab and ustekinumab); CD3 (e.g., muromonab-CD3, otelixizumab, teplizumab, visilizumab); CD4 (e.g., clenoliximab, keliximab and zanolimumab); CD11a (e.g., efalizumab); CD18 (e.g., erlizumab); CD20 (e.g., afutuzumab, ocrelizumab, pascolizumab); CD23 (e.g., lumiliximab); CD40 (e.g., teneliximab, toralizumab); CD62L/L-selectin (e.g., aselizumab); CD80 (e.g., galiximab); CD147/basigin (e.g., gavilimomab); CD154 (e.g., ruplizumab); BLyS (e.g., belimumab); CTLA-4 (e.g., ipilimumab, tremelimumab); CAT (e.g., bertilimumab, lerdelimumab, metelimumab); integrin (e.g., natalizumab); IL-6 receptor (e.g., tocilizumab); LFA-1 (e.g., odulimomab); and IL-2 receptor/CD25 (e.g., basiliximab, daclizumab, inolimomab).

Natural antibodies of the recipient may be eliminated by organ perfusion, and/or transplantation of tolerance-inducing bone marrow.

In one embodiment, a recipient is treated with a preparation of horse anti-human thymocyte globulin (ATG) injected intravenously (e.g., at a dose of approx. 25-100 mg/kg, e.g., 50 mg/kg, e.g., at days −3, −2, −1 prior to transplantation). The antibody preparation eliminates mature T cells and natural killer cells. The ATG preparation also eliminates natural killer (NK) cells. Anti-human ATG obtained from any mammalian host can also be used. In addition, if further T cell depletion is indicated, the recipient may be treated with a monoclonal anti-human T cell antibody, such as LoCD2b (Immerge BioTherapeutics, Inc., Cambridge, Mass.). For bone marrow transplant, the recipient can be administered low dose radiation. In some cases, the recipient can be treated with an agent that depletes complements, such as cobra venom factor (e.g., at day −1).

In some embodiments, maintenance therapy (e.g., beginning immediately prior to, and continuing for at least a few days after transplantation) includes treatment with a human anti-human CD154 mAb. Mycophenolate mofetil (MMF) may be administered to maintain the whole blood levels. Methylprednisolone may also be administered, beginning on the day of transplantation, tapering thereafter over the next 3-4 weeks.

Various agents useful for supportive therapy (e.g., at days 0-14) include anti-inflammatory agents such as prostacyclin, dopamine, ganiclovir, levofloxacin, cimetidine, heparin, antithrombin, erythropoietin, and aspirin.

In some embodiments, donor stromal tissue is administered. It may be obtained from fetal liver, thymus, and/or fetal spleen, may be implanted into the recipient, e.g., in the kidney capsule. Thymic tissue can be prepared for transplantation by implantation under the autologous kidney capsule for revascularization. Stem cell engraftment and hematopoiesis across disparate species barriers may be enhanced by providing a hematopoietic stromal environment from the donor species. The stromal matrix supplies species-specific factors that are required for interactions between hematopoietic cells and their stromal environment, such as hematopoietic growth factors, adhesion molecules, and their ligands.

As liver is the major site of hematopoiesis in the fetus, fetal liver can also serve as an alternative to bone marrow as a source of hematopoietic stem cells. The thymus is the major site of T cell maturation. Each organ includes an organ specific stromal matrix that can support differentiation of the respective undifferentiated stem cells implanted into the host. Thymic stromal tissue can be irradiated prior to transplantation. As an alternative or an adjunct to implantation, fetal liver cells can be administered in fluid suspension.

Bone marrow cells (BMC), or another source of hematopoietic stem cells, e.g., a fetal liver suspension, of the donor can be injected into the recipient. Donor BMC home to appropriate sites of the recipient and grow contiguously with remaining host cells and proliferate, forming a chimeric lymphohematopoietic population. By this process, newly forming B cells (and the antibodies they produce) are exposed to donor antigens, so that the transplant will be recognized as self. Tolerance to the donor is also observed at the T cell level in animals in which hematopoietic stem cell, e.g., BMC, engraftment has been achieved. The use of xenogeneic donors allows the possibility of using bone marrow cells and organs from the same animal, or from genetically matched animals.

The practice of the present invention may employ certain techniques which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. 15 Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

The following is an example of the present invention and is not to be construed as limiting.

Example 1 Generating Transgenic Donor Animals

The production of genetically modified pigs by somatic cell nuclear transfer (SCNT) have previously been reported. Petersen et al, Xenotransplantation. 2009, 16(6):486-95. Yan et al, Production of transgenic pigs over-expressing the antiviral gene IL-3R, Cell Regeneration 2014, 3:11. Lai et al., Generation of cloned transgenic pigs rich in omega-3 fatty acids. Nat. Biotechnol. 2006; 24:435-436. Yang et al., Expression of Huntington's disease protein results in apoptotic neurons in the brains of cloned transgenic pigs. Hum. Mol. Genet. 2010; 19:3983-3994. Yang et al., Generation of PPARγ mono-allelic knockout pigs via zinc-finger nucleases and nuclear transfer cloning. Cell Res. 2011; 21:979-982.

In this study, we will use SCNT to produce transgenic pigs with their endogenous pig IL-3R gene modified to contain at least one conditional knockout allele. The transgenic pigs will also have the human IL-3R gene knocked in which will be expressed under the control of the pig native regulatory sequence of the pig IL-3R gene when the pig IL-3R gene is knocked out. In other words, the target gene here is the pig IL-3R gene; and the transgene is the human IL-3R gene.

Vector Construction and Selection of Transgenic Donor Cells

Primary pig fetal fibroblasts will be isolated from a 25 day-fetus of a female MGH miniature pig, and cultured in Dulbecco's modified Eagle's medium (DMEM, HyClone, Logan, Utah, USA) supplemented with 15% fetal bovine serum (FBS, HyClone, Logan, Utah, USA) and 1% (v:v) penicillin/streptomycin (10,000 U/ml penicillin, 10,000 μm/ml streptomycin; GIBCO-BRL, Grand Island, N.Y., USA) at 39° C. in an incubator with 5% $CO_2$. Cultured fibroblasts will then be stimulated with 1000 U/ml IFN-α (PeproTech, Rocky Hill, N.J., USA) for about 6 hours.

The conditional knockout gene of the pig IL-3R (e.g., pig IL-3R gene flanked by two loxP sites) and the human IL-3R gene will then be inserted into a vector, for example pVAX1 (Invitrogen, Carlsbad, Calif., USA). An inducible Cre recombinase gene can be targeted to the ROSA26 locus and constructed in a separated vector. The final constructs will be confirmed by sequencing.

The vectors are then transfected into the fibroblast cells, for example using Lipofectamine 2000 (Invitrogen, Carlsbad, Calif., USA) or by electroporation (Gene Pulser Xcell, Bio-rad, Hercules, Calif., USA). Transfected pig cells are harvested and lysed 48 hours later. Expression of the transgenes may be be detected, for example, by antibodies. Transgenes can also be detected by PCR.

The transfected pig cells may be then split 1:10 into fresh culture medium after transfection and cultured for approximately 2 weeks. The surviving cell colonies that express the transgenes can be selected for example using PCR, and propagated in a fresh 48-well plate. Colonies that proliferate well will then expanded and screened for the presence of the transgenes. The positive colonies can be frozen in small aliquots.

Prior to SCNT, transgenic cells are thawed and cultured until they reached sub-confluence. For production of transgenic pigs, SCNT can be performed as described in Yang et al., Expression of Huntington's disease protein results in apoptotic neurons in the brains of cloned transgenic pigs, Hum. Mol. Genet. 2010, 19:3983-3994. The reconstructed embryos are then surgically transferred into the oviduct of a surrogate female pig on the first day of standing estrus. The pregnancy status is monitored, for example using an ultrasound scanner between 30-35 days post-transplantation. Some embryos are cultured for 6 days to test the blastocyst formation rate as well as developmental ability.

Identification of Transgenic Pigs

Genomic DNA will be obtained from newborn cloned pigs for PCR analysis, and primers used to amplify the human IL-3R gene, conditional pig IL-3R knockout allele, and the Cre gene or fragments thereof. Total RNA will be extracted from fibroblasts isolated for example from the ear tissues of newborn cloned piglets using the RNeasy Mini Kit (Qiagen, Valencia, Calif., USA), subjected to reverse transcription (PrimeScript RT Master Mix, Takara, Dalian, China) and real time RT-PCR (SYBR Premix Ex Taq™, Takara, Dalian, China) to determine the expression levels of human IL-3R mRNA after knock out of the pig IL-3R gene. RNA samples from 1-3 newborn natural breeding inbred MGH miniature piglets can be used as controls. Western blot will be used to detect the expression of human IL-3R protein in the transgenic pigs after knock out of the pig IL-3R gene, using fibroblast lysates and organ lysates of transgenic pig and non-transgenic pig control. Xenotransplantation. 2009 November-December; 16(6):486-95.

As used herein, the term "transgene" is a gene partly or entirely heterologous, i.e., foreign, to the donor/host (e.g., swine) animal or a cell of the mammalian species of the donor animal into which it is introduced. Besides exons, a transgene may include any other nucleic acid sequences, such as introns and/or regulatory sequence, that may be necessary for optimal expression of the transgene. As used herein, the term "transgenic cell" refers to a cell containing a transgene.

As used herein, the term "xenogeneic transgene" refers to a gene from a first species that is inserted into the genome of a second species.

As used herein, the terms "xenogeneic transgenic cell" refers to a cell containing a transgene from another species.

A donor animal refers to a mammal of a first mammalian species. The donor animal is the donor of cells, tissues, and/or organs for the xenotransplantation. A donor animal is also referred to as the host animal to the transgene(s) it may carry. The recipient of the xenotransplantation is a mammal of a second mammalian species.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description is offered by way of illustration only and not as a limitation.

Sequences

SEQ ID NO: 1
ATAACTTCGTATAGCATACATTATACGAAGTTAT

SEQ ID NO: 2
ATAACTTCGTATANNNTANNNTATACGAAGTTAT

---

What is claimed is:

1. A method of supplying a graft from a donor mammal of a first species for transplant in a recipient mammal of a second species, the method comprising the steps of:
 (A) providing a transgenic mammal of the first species, comprising an engineered genome having, from 5' to 3':
  (i) at least one conditional knockout allele of a target gene of the first species, wherein the conditional knockout allele comprises from 5' to 3':
   (a) a first recombinase recognition site;
   (b) a target gene of the first species at its natural genomic locus of the first mammalian species;
   (c) a stop codon;
   (d) a second recombinase recognition site; and
  (ii) a transgene of the second species,
 (B) inducing knockout of at least one conditional knockout allele of the target gene in the donor mammal about 6 months to about 1 day prior to supplying the graft, wherein the target gene encodes a cytokine receptor or CD47 of the first species,
 (C) expressing the transgene of the second species upon knockout of the target gene, wherein the transgene:
  (i) is a homolog of the target gene;
  (ii) encodes a cytokine receptor or CD47 of the second species; and
  (iii) is expressed under control of the native regulatory elements of the target gene when the target gene is knocked out; and
 (D) supplying the graft from the donor mammal for transplant,
wherein the donor mammal expresses the target gene before knockout of the target gene,
wherein the first species is swine, and
wherein the second species is human.

2. The method of claim 1, wherein the conditional knockout allele is flanked by two LoxP sequences and is knocked out by an inducible Cre recombinase.

3. The method of claim 2, wherein the LoxP sequences are SEQ ID NO:1.

4. The method of claim 2, wherein expression of the inducible Cre recombinase is under control of an inducible promoter.

5. The method of claim 4, wherein the inducible promoter is induced by a drug.

6. The method of claim 2, wherein the Cre recombinase is induced by translocating to the nucleus of a cell upon addition of a drug.

7. The method of claim 5, wherein the drug is selected from the group consisting of doxycycline, tetracycline, RU486, and tamoxifen.

8. The method of claim 1, wherein the conditional knockout allele of the target gene comprises a nucleic acid sequence at least 90% identical to the sequence of wildtype allele of the target gene of the first species.

9. The method of claim 1, wherein the graft comprises cells, a tissue or an organ selected from the group consisting of a heart, a kidney, a liver, a pancreas, a lung, an intestine, skin, a small bowel, a trachea, a cornea, and combinations thereof.

10. The method of claim 1, wherein the target gene encodes CD47.

11. The method of claim 1, wherein the target gene encodes the cytokine receptor.

12. The method of claim 11, wherein the cytokine receptor is Interleukin-3 (IL-3) receptor.

* * * * *